United States Patent
Chen et al.

(10) Patent No.: US 12,239,522 B2
(45) Date of Patent: Mar. 4, 2025

(54) PROSTHETIC HEART VALVE PACKAGING

(71) Applicant: Edwards Lifesciences Corporation, Irvine, CA (US)

(72) Inventors: Harvey H. Chen, Irvine, CA (US); Myron Howanec, Jr., Corona, CA (US); Robert Pozzo, Jr., Lake Forest, CA (US); Curt G. Corte, Wrightwood, CA (US); Laura Elizabeth Wasson, Silverado, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 174 days.

(21) Appl. No.: 17/649,532

(22) Filed: Jan. 31, 2022

(65) Prior Publication Data
US 2022/0151759 A1     May 19, 2022

Related U.S. Application Data

(63) Continuation of application No. PCT/US2020/044701, filed on Aug. 3, 2020.

(60) Provisional application No. 62/882,415, filed on Aug. 2, 2019.

(51) Int. Cl.
*A61F 2/24* (2006.01)
*A61F 2/00* (2006.01)

(52) U.S. Cl.
CPC .......... *A61F 2/0095* (2013.01); *A61F 2/2412* (2013.01)

(58) Field of Classification Search
CPC .... A61F 2/0095; A61F 2/2412; A61F 2/2427; A61F 2/24

USPC ................................................ 206/438, 363
See application file for complete search history.

(56) References Cited

U.S. PATENT DOCUMENTS

| | | |
|---|---|---|
| 4,011,947 A | 3/1977 | Sawyer |
| 4,101,031 A | 7/1978 | Cromie |
| 4,182,446 A | 1/1980 | Penny |
| 4,211,325 A | 7/1980 | Wright |
| 4,697,703 A | 10/1987 | Will |
| 4,801,015 A | 1/1989 | Lubock et al. |
| 5,167,223 A | 12/1992 | Koros et al. |
| 5,236,450 A | 8/1993 | Scott |
| 5,336,616 A | 8/1994 | Livesey et al. |

(Continued)

FOREIGN PATENT DOCUMENTS

WO    2008035337 A2    3/2008

*Primary Examiner* — Steven A. Reynolds
(74) *Attorney, Agent, or Firm* — Darren Franklin; Nathan Lee; Sheppard, Mullin, Richter & Hampton LLP

(57) ABSTRACT

A packaging assembly for storing a bioprosthetic heart valve is disclosed. The packaging assembly can include a subassembly comprising a valve holder configured to hold the bioprosthetic heart valve, and a clip configured to receive a shaft of the valve holder. The clip can comprise a body having an outer periphery and opposing inner edges. The opposing inner edges can define a slot in the body for receiving the shaft of the valve holder. The slot can be open at a first end of the body and extend, along a longitudinal axis of the body, from the first end to a docking aperture. The clip can further comprise a compliance feature in an interference-fit area of the slot adjacent to the docking aperture. The compliance feature can comprise a cutout adjacent to each of the opposing inner edges such that each of the opposing inner edges defines a beam within the interference-fit area.

27 Claims, 15 Drawing Sheets

(56) References Cited

U.S. PATENT DOCUMENTS

| | | | |
|---|---|---|---|
| 5,480,425 A | 1/1996 | Ogilive | |
| 5,531,785 A | 7/1996 | Love et al. | |
| 5,560,487 A | 10/1996 | Starr | |
| 5,578,076 A | 11/1996 | Krueger et al. | |
| 5,582,607 A | 12/1996 | Lackman | |
| 5,615,770 A | 4/1997 | Applebaum et al. | |
| 5,690,226 A | 11/1997 | N'Guyen | |
| 5,720,391 A * | 2/1998 | Dohm | A61F 2/0095 206/583 |
| 5,776,187 A | 7/1998 | Krueger et al. | |
| 5,800,531 A * | 9/1998 | Cosgrove | A61F 2/2412 623/2.11 |
| 5,823,342 A | 10/1998 | Caudillo et al. | |
| 5,868,253 A * | 2/1999 | Krueger | A61F 2/0095 206/583 |
| 5,980,569 A | 11/1999 | Scirica | |
| 5,984,959 A | 11/1999 | Robertson et al. | |
| 6,090,138 A | 7/2000 | Chasak et al. | |
| 6,126,007 A * | 10/2000 | Kari | A61F 2/2427 206/583 |
| 6,197,053 B1 | 3/2001 | Cosgrove et al. | |
| 6,199,696 B1 | 3/2001 | Lytle et al. | |
| 6,346,094 B2 | 2/2002 | West et al. | |
| 6,416,547 B1 * | 7/2002 | Erickson | A61F 2/0095 623/2.11 |
| 6,534,004 B2 | 3/2003 | Chen et al. | |
| 6,591,998 B2 | 7/2003 | Haynes et al. | |
| 6,723,122 B2 | 4/2004 | Yang et al. | |
| 6,736,845 B2 | 5/2004 | Marquez et al. | |
| 6,966,925 B2 | 11/2005 | Stobie | |
| 7,389,874 B2 | 6/2008 | Quest et al. | |
| 7,699,168 B2 * | 4/2010 | Ryan | A61F 2/0095 623/2.1 |
| 7,712,606 B2 | 5/2010 | Salahieh et al. | |
| 7,866,468 B2 | 1/2011 | Kyritsis | |
| 8,652,145 B2 | 2/2014 | Maimon et al. | |
| 8,869,982 B2 * | 10/2014 | Hodshon | A61F 2/2412 206/363 |
| 2002/0120328 A1 | 8/2002 | Pathak et al. | |
| 2003/0070944 A1 | 4/2003 | Nigam | |
| 2005/0241981 A1 | 11/2005 | Gupta et al. | |
| 2006/0015177 A1 * | 1/2006 | Quest | A61F 2/2427 623/2.11 |
| 2006/0155363 A1 | 7/2006 | LaDuca et al. | |
| 2006/0195183 A1 | 8/2006 | Navia et al. | |
| 2008/0082163 A1 | 4/2008 | Woo | |
| 2008/0177381 A1 | 7/2008 | Navia et al. | |
| 2008/0230423 A1 * | 9/2008 | Loeffler | A61B 90/90 606/300 |
| 2009/0130162 A2 | 5/2009 | Pathak et al. | |
| 2009/0164005 A1 | 6/2009 | Dove et al. | |
| 2011/0147251 A1 * | 6/2011 | Hodshon | A61F 2/2412 206/438 |
| 2011/0198244 A1 * | 8/2011 | Murad | A61F 2/0095 206/210 |
| 2011/0214398 A1 * | 9/2011 | Liburd | B65D 77/26 53/467 |
| 2012/0290079 A1 * | 11/2012 | Murad | A61F 2/2412 623/2.17 |
| 2013/0325111 A1 | 12/2013 | Campbell et al. | |
| 2016/0128819 A1 * | 5/2016 | Giordano | A61F 2/2427 623/2.11 |
| 2017/0056149 A1 | 3/2017 | Rajpara et al. | |

\* cited by examiner

PROSTHETIC HEART VALVE PACKAGING

CROSS-REFERENCE TO RELATED APPLICATIONS

This application is a continuation of International Patent Application No. PCT/US2020/044701, filed Aug. 3, 2020, which claims the benefit of U.S. Patent Application No. 62/882,415, filed on Aug. 2, 2019, the entire disclosures all of which are incorporated by reference for all purposes.

TECHNICAL FIELD

This invention relates generally to packaging for prosthetic heart valves and, more particularly, to a packaging sub-assembly comprising a clip having a compliance feature.

BACKGROUND

Heart valve disease continues to be a significant cause of morbidity and mortality. Currently, the primary treatment of heart valve disease is heart valve replacement. A prosthetic heart valve can be environmentally sensitive and must be packaged to protect the valve from impacts and contamination during transportation. It is important, therefore, for packaging to provide a structure that can protect the heart valve, but also allow the valve to be easily removed without damage or contamination.

Manufacturers have suspended bioprosthetic heart valves within packaging containers for shipping and storage prior to use in the operating room. The valves have been stabilized with various structures, including, for example, a valve holder and a retainer clip having a radial slot for receiving a shaft of the valve holder (as shown, for example, in U.S. Pat. No. 9,539,080), and a packaging sleeve that fits closely within a jar and has a clip structure for securing a valve holder (as shown, for example, in U.S. Pat. Nos. 8,839,957; 9,918,836; and 9,295,539).

Current use of an interference fit between the retainer clip and the valve holder has had mixed success. For example, some valves have become dislodged from the retainer clip during shipping simulation, while other valves have become stuck or difficult to remove from the retainer clip. Adjusting the interference fit is a challenge, as a minuscule change in the interference feature can significantly affect the force required to release the valve holder from the retainer clip.

It should be appreciated that there is a need for an improved heart-valve packaging system that is configured to securely maintain a bioprosthetic heart valve within the packaging system, while allowing for easy removal of the heart valve from the packaging system without damage or contamination. The present invention fulfills this need and provides further related advantages.

SUMMARY

The present invention is embodied in a packaging assembly for storing a bioprosthetic heart valve. In one embodiment, the packaging assembly includes a sub-assembly comprising a valve holder configured to hold the bioprosthetic heart valve, and a clip configured to receive a shaft of the valve holder. The shaft has a shaft width, and the clip comprises a body having an outer periphery and opposing inner edges. The opposing inner edges define a slot in the body for receiving the shaft of the valve holder. The slot is open at a first end of the body and extends, along a longitudinal axis of the body, from the first end to a docking aperture. The clip further comprises a compliance feature in an interference-fit area of the slot adjacent to the docking aperture. In one embodiment, a slot width between the opposing inner edges of the body in the interference-fit area is less than the shaft width. In another embodiment, the compliance feature comprises a cutout adjacent to each of the opposing inner edges such that each of the opposing inner edges defines a beam within the interference-fit area.

In one embodiment, the body can be substantially planar. In another embodiment, the cutout adjacent to each of the opposing inner edges can be oblong. In a further embodiment, the slot width can decrease from the first end of the body to the interference-fit area. In an additional embodiment, the clip can comprise a molded polymer. In yet another embodiment, the clip can comprise a high-density polyethylene or an acetal resin or a polyoxymethylene, such as DELRIN® (manufactured by Dupont).

In one embodiment, the beam defined by each of the opposing inner edges can be a fixed beam, a cantilevered beam, or a simply-supported beam. In an additional embodiment, the beam defined by each of the opposing inner edges can have an average beam width from about 0.5 mm to about 2 mm.

In one embodiment, the shaft of the valve holder can have a substantially circular cross-section. In another embodiment, the valve holder can further comprise a cap coupled to a first end of the shaft and an engagement structure coupled to a second end of the shaft, wherein the engagement structure is configured to removably couple to the bioprosthetic heart valve. In a further embodiment, the shaft can separate the cap and the engagement structure. In an additional embodiment, the engagement structure can comprise a plurality of legs. In yet another embodiment, the plurality of legs can be outwardly and downwardly angled.

In one embodiment, the packaging assembly can further comprise a storage tray having a stepped ledge surrounding a cavity. In another embodiment, the clip's body can be shaped to rest on the stepped ledge of the storage tray such that the valve holder's engagement structure is suspended within the cavity of the storage tray when the valve holder is docked within the clip's docking aperture. In a further embodiment, the packaging assembly can further comprise a gas-permeable lid coupled to an upper surface of the storage tray.

The present invention is also embodied in a holding assembly comprising a valve holder configured to hold a bioprosthetic heart valve, and a clip configured to receive a shaft of the valve holder. The shaft has a shaft width, and the clip comprises a body having an outer periphery and opposing inner edges. The opposing inner edges define a slot in the body for receiving the shaft of the valve holder. The slot is open at a first end of the body and extends, along a longitudinal axis of the body, from the first end to a docking aperture. The clip further comprises a compliance feature in an interference-fit area of the slot adjacent to the docking aperture. In one embodiment, a slot width between the opposing inner edges of the body in the interference-fit area is less than the shaft width. In another embodiment, the compliance feature comprises a first cutout adjacent to one of the opposing inner edges such that the one of the opposing inner edges defines a beam within the interference-fit area.

In one embodiment, the body can be substantially planar. In another embodiment, the beam defined by one of the opposing inner edges can be a fixed beam, a cantilevered beam, or a simply-supported beam. In a further embodiment, the compliance feature can further comprise a second cutout adjacent to another of the opposing inner edges such that each of the opposing inner edges defines a beam within the interference-fit area.

In another separate embodiment, a packaging assembly for storing a bioprosthetic heart valve is provided. The packaging assembly can comprise a valve holder and a clip. The valve holder can be configured to hold the bioprosthetic heart valve. The valve holder can comprise a shaft having a shaft width. The clip can be configured to receive the shaft of the valve holder. The clip can comprise a body having first and second ends and peripheral edges extending between the first and second ends. The clip can further comprise a passageway in the body for receiving the shaft of the valve holder. The passageway can comprise an opening at a first end of the body, a terminal docking end within the body and opposing inner edges defining a first slot between the opening and the terminal docking end. The first slot can have a width $W_2$. The clip can further comprise a release mechanism. The release mechanism can comprise holds provided on the peripheral edges of the body and a second set of one or more slots provided between the holds. The second set of one or more slots can each have a width $W_3$, an opening at the second end of the body and a slot end within the body. The holds can be configured to be compressible towards one another to decrease the width $W_3$ of each one of the second set of one or more slots. Decreasing the width $W_3$ of each one of the second set of the one or more slots can increase the width $W_2$ of the first slot to permit insertion and removal of the valve holder to and from the slot end.

In one embodiment, the clip can be made of a resilient material. The resilient material can be a molded polymer. The molded polymer can be a high-density polyethylene or an acetal resin or a polyoxymethylene, such as DELRIN® (manufactured by Dupont).

In one embodiment, the holds can have a concave surface.

In one embodiment, the release mechanism can comprise two slots. In one embodiment, a distance $d_1$ between the openings of the release mechanism slots can be greater than a distance $d_2$ between the release mechanism slot ends.

In one embodiment, the clip can further comprise a compliance feature in an interference-fit area of the slot that is adjacent to the terminal docking end. A width of the slot in the interference-fit area can be smaller than the shaft width. In one embodiment, the compliance feature can comprise a cutout adjacent to each of the opposing inner edges in the interference-fit area such that each of the opposing inner edges defines a beam. In one embodiment, the beam defined by each of the opposing inner edges can be a fixed beam, a cantilevered beam, or a simply-supported beam.

In one embodiment, the packaging assembly can further comprise a storage tray having a stepped ledge surrounding a cavity. The clip's body can be shaped to rest on the stepped ledge of the storage tray such that the valve holder's engagement structure can be suspended within the cavity of the storage tray when the valve holder is docked within the clip's docking aperture. The storage tray can comprise a gas-permeable lid coupled to an upper surface of the storage tray.

In yet a further embodiment, a packaging assembly for storing a bioprosthetic heart valve is provided. The packaging assembly for storing a bioprosthetic heart valve can comprise a valve holder and a clip. The valve holder can be configured to hold the bioprosthetic heart valve and can comprise a shaft and a shaft width. The clip can be configured to receive a shaft of the valve holder. The clip can comprise a body having first and second ends and peripheral edges extending between the first and second ends. The clip can further comprise a passageway in the body for receiving the shaft of the valve holder, wherein the passageway can comprise an opening at a first end of the body, opposing inner edges defining a slot and a terminal docking end within the body. The clip can further include a flap hingedly coupled to the body and configured to be actuated between an open position and a closed position. In the open position, the flap can be hingedly positioned away from the slot to allow the shaft of the valve holder to freely slide within the passageway between the opening and the terminal docking end. In the closed position, the flap covers at least a portion of the slot to secure the valve holder in place when positioned in the terminal docking end.

In one embodiment, one or both of the clip and the flap can be made of a resilient material. The resilient material can be a molded polymer. The molded polymer can be a high-density polyethylene or an acetal resin or a polyoxymethylene, such as DELRIN® (manufactured by Dupont).

In one embodiment, the flap can be sized and shaped to cover or block a portion of the slot to secure the shaft of the valve holder at the terminal docking end and prevent the shaft from sliding out of the opening when the flap is in the closed position. In one embodiment, the flat does not cover the terminal docking end. In one embodiment, the flap can further comprise a protrusion to allow grasping to open and close the flap. In one embodiment, the passageway width can be no smaller than the shaft width.

In one embodiment, the clip can further comprise a stepped ledge disposed within one or both of the slot and the terminal docking end. The flap can rest on the stepped ledge in the closed position.

In one embodiment, the shaft of the valve holder can be retained within the terminal docking end without requiring an interference fit within the passageway.

In one embodiment, the packaging assembly can further comprise a storage tray having a stepped ledge surrounding a cavity. The clip's body can be shaped to rest on the stepped ledge of the storage tray such that the valve holder's engagement structure is suspended within the cavity of the storage tray when the valve holder is docked within the clip's docking aperture. The storage tray can further comprise a gas-permeable lid coupled to an upper surface of the storage tray.

Each feature or concept outlined above is independent, and can be combined with the other features or concepts outlined above or with any other feature or concept disclosed in this application. Other features and advantages of the invention should become apparent from the following description of the preferred embodiments, taken in conjunction with the accompanying drawings, which illustrate, by way of example, the principles of the invention.

DETAILED DESCRIPTION

Figure 1:
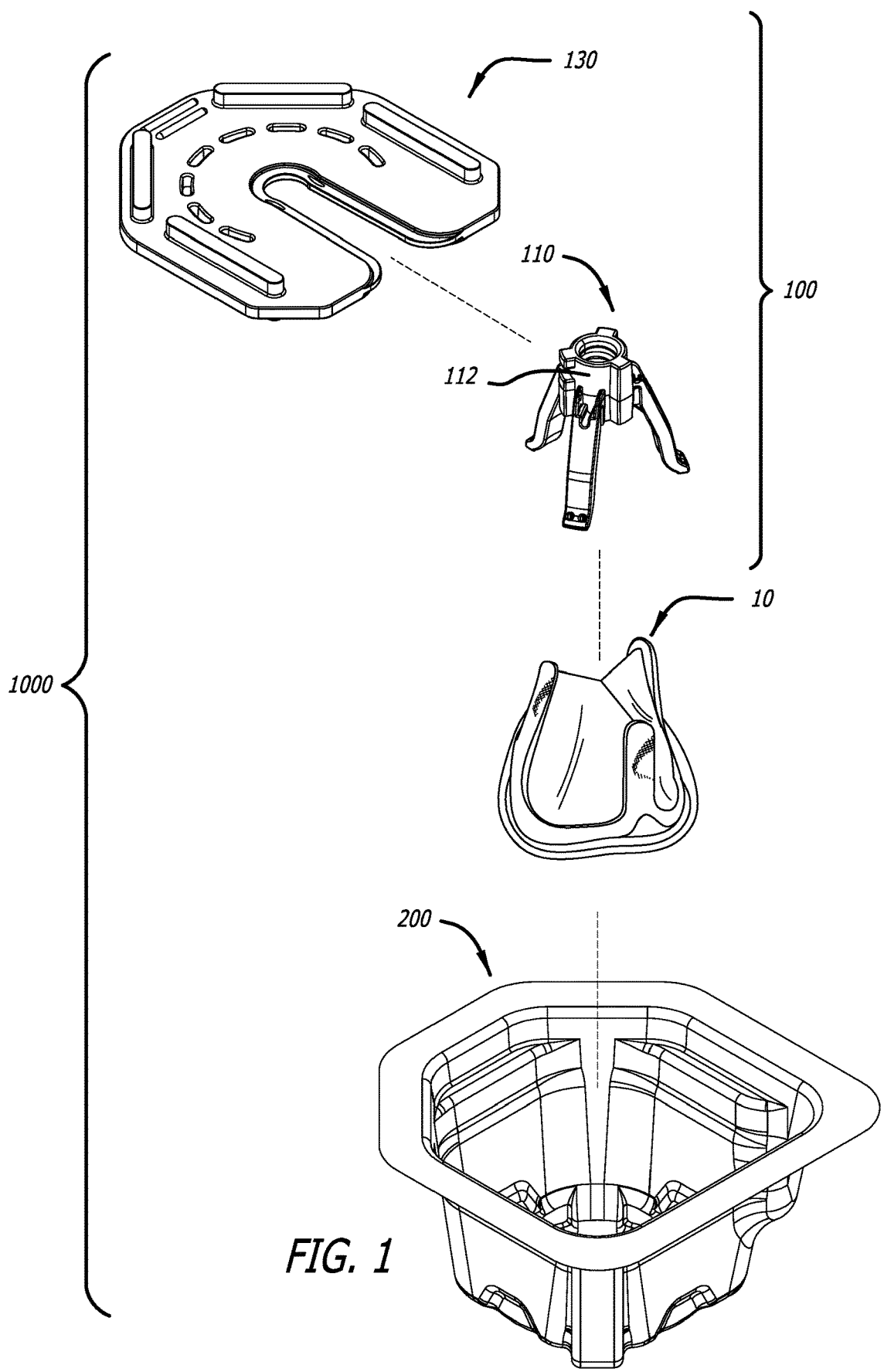
FIG. 1 is an exploded perspective view of a packaging assembly for storing a bioprosthetic heart valve, in accordance with one embodiment.

With reference now to FIG. 1 of the illustrative drawings, there is shown a packaging assembly 1000 for storing a bioprosthetic heart valve 10. The packaging assembly 1000 can include a sub-assembly 100 comprising a valve holder no configured to hold the bioprosthetic heart valve 10, and a clip 130 configured to receive a shaft 112 of the valve holder 110. As will be discussed in more detail below, the sub-assembly 100 holding the bioprosthetic heart valve 10 can be placed into a container such as a jar (not shown) or a storage tray 200, and further processed for storage and shipment.

Figure 2:
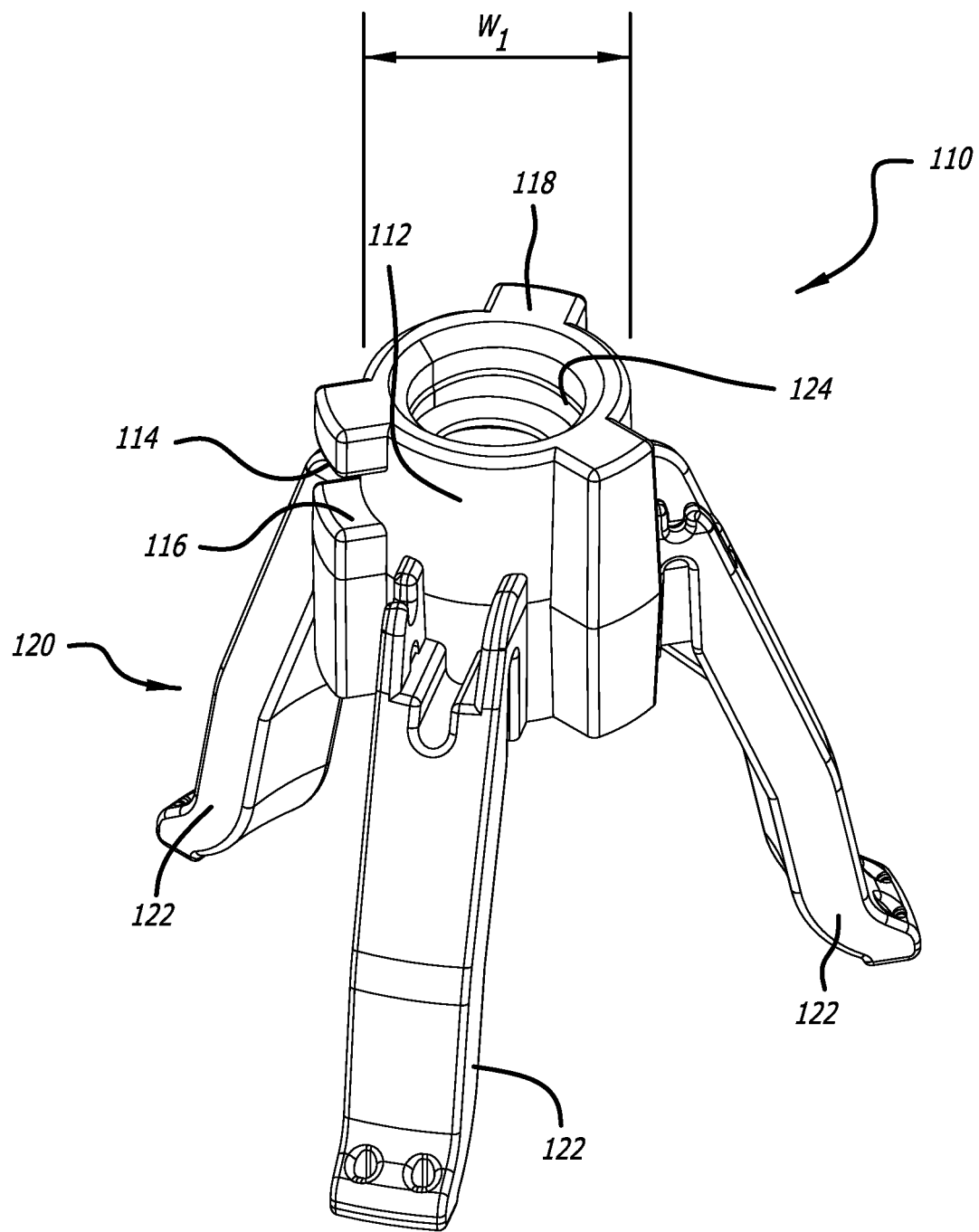
FIG. 2 is a perspective view of a valve holder in accordance with one embodiment.

With reference to FIG. 2, the valve holder no can comprise a cap 118 coupled to a first end 114 of the shaft 112 and an engagement structure 120 coupled to a second end of the shaft 112. In one embodiment, the cap 118 can comprise a bore with internal threads 124, the shaft 112 can have a shaft width $W_1$ and a substantially circular-cross-section, and the engagement structure 120 can be configured to removably couple to the bioprosthetic heart valve 10. For example, the engagement structure 120 illustrated in FIG. 2 comprises a plurality of legs 122 that are outwardly and downwardly angled. The legs 122 can be arranged to contact and engage cusp regions of the heart valve 10, as is known in the art. Although not shown, one configuration for connecting the legs 122 to the heart valve 10 includes attachment sutures that loop through suture-permeable material in the heart valve 10 and tie off on the valve holder 110. During implant, a surgeon can manipulate a handle (not shown) screwed into the threaded bore 124 and advance the heart valve 10 into implant position. Once in position, the surgeon can sever the attachment sutures coupling the valve holder 110 to the heart valve 10, and remove the valve holder no and the handle.

In accordance with one exemplary embodiment, a clip that provides an interference-fit with a valve holder is provided. With reference now to FIGS. 3A-3F, the clip 130 can comprise a substantially planar body 132 having an outer periphery 134 and opposing inner edges 136A, 136B. The opposing inner edges 136A, 136B can define a slot 138 in the body 132 for receiving the shaft 112 of the valve holder 110. The slot 138 can be open at a first end 140 of the body 132 and can extend, along a longitudinal axis l of the body 132, from the first end 140 to a docking aperture 142.

Figure 4:
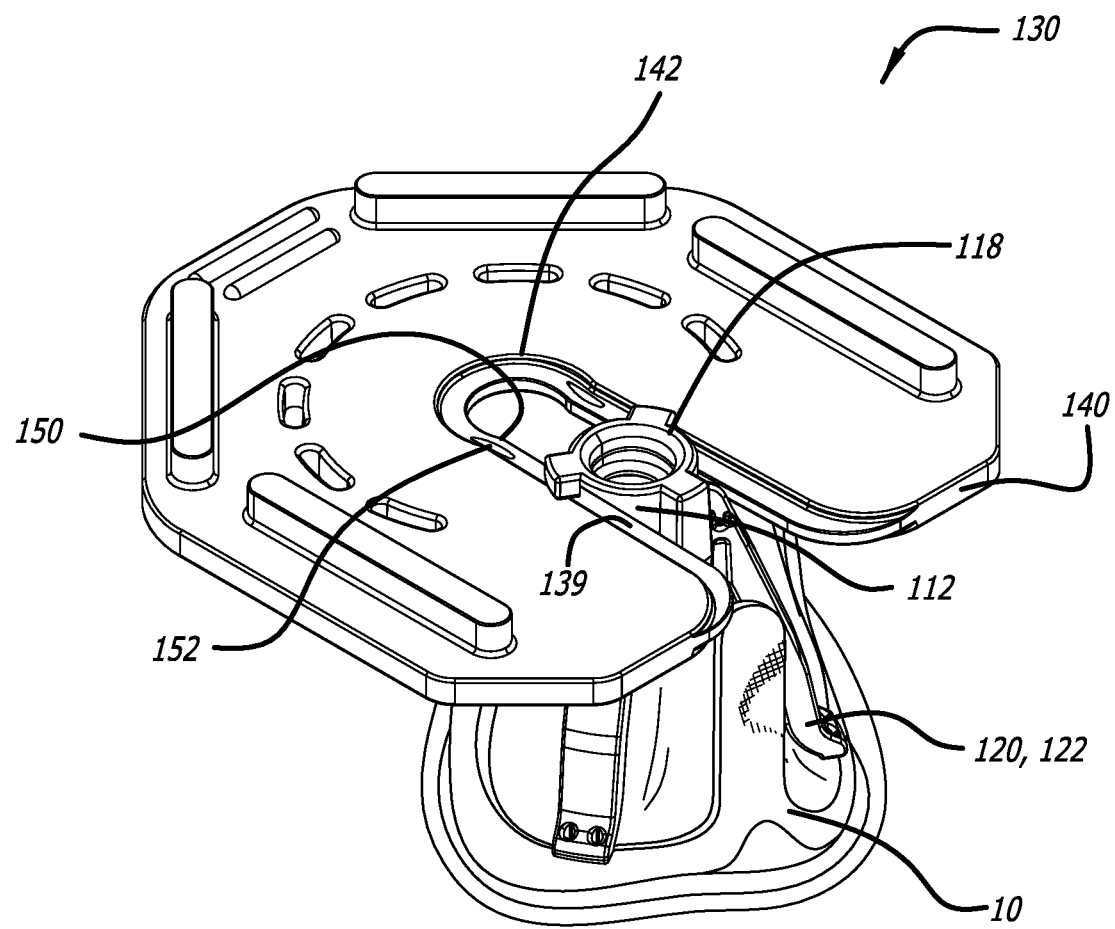
FIG. 4 illustrates a bioprosthetic heart valve and valve holder being moved along a slot in the body of the clip in accordance with one embodiment.

In one embodiment, the slot 138 can include an interference-fit area 150 adjacent to the docking aperture 142. A slot width $W_2$ between the opposing inner edges 136A, 136B of the body 132 can decrease from the first end 140 of the body 132 to the interference-fit area 150. In one embodiment, the slot width $W_2$ in the interference-fit area 150 can be less than the valve holder's no shaft width $W_1$. As such, when the shaft 112 of the valve holder no is pushed inward along the slot 138 (as illustrated in FIG. 4), the shaft 112 will push against the opposing inner edges 136A, 136B in the interference-fit area 150 before snapping into (or out of) the docking aperture 142.

The interference-fit area 150 is provided to maintain the valve holder 110 within the docking aperture 142, during processing, storage, and shipment—until the valve holder 110 is deliberately removed by the physician. The interference-fit area 150 should maintain the valve holder no in the docking aperture 142 during transportation, and also allow for the easy removal of the valve holder 110 in the operating room. Accordingly, the force required to move the valve holder no past the interference-fit area 150 should be from about 3 N to about 13 N. This interference force is set by the interference width, which is the difference between the shaft width W, and the slot width $W_2$ in the interference-fit area 150. The interference width might, for example, have a tolerance range of about ±125 μm. However, adjusting the interference width has been a challenge as a mere 25 μm to 50 μm change can significantly affect the force required to release the valve holder 110 from the clip 130. As a result, current use of an interference fit between the clip 130 and the valve holder 110 has had mixed success. For example, some valve holders 110 have become dislodged from the clip 130 during shipping simulation, while other valve holders 110 have become stuck or difficult to remove from the clip 130.

In one embodiment, the interference width can be in the range of about 5 μm or more, about 10 μm or more, about 15 μm or more, about 20 μm or more, about 25 μm or more, about 30 μm or more, about 35 μm or more, about 40 μm or more, about 45 µm or more, about 50 µm or more, about 55 µm or more, about 60 µm or more, about 65 µm or more, about 70 µm or more, about 75 µm or more, about 80 µm or more, about 85 µm or more, about 90 µm or more, about 95 µm or more, about 100 µm or more, about 105 µm or more, about 110 µm or more, about 115 µm or more, about 120 µm or more, and about 125 µm or more. The interference width can also be in a range between and including any two of the foregoing values.

Figure 3A:
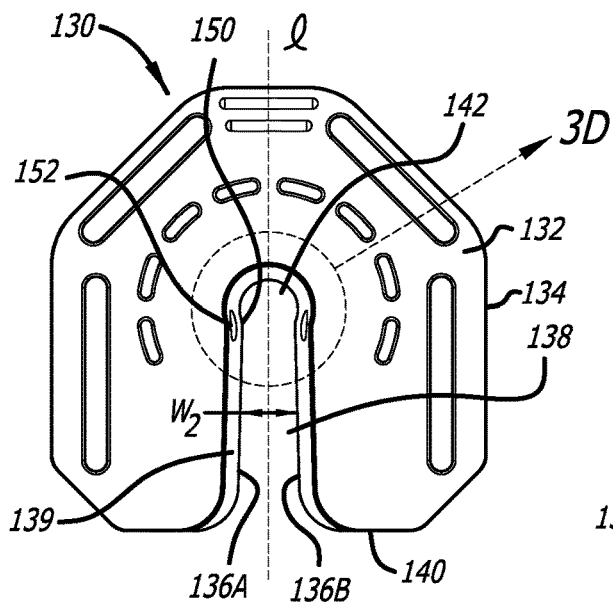
FIG. 3A is a top orthogonal view of a clip in accordance with one embodiment.
Figure 3B:
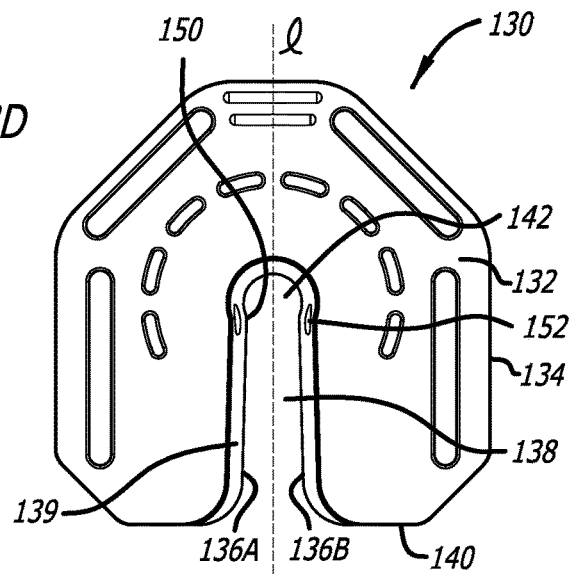
FIG. 3B is a bottom orthogonal view of the clip of FIG. 3A.
Figure 3C:
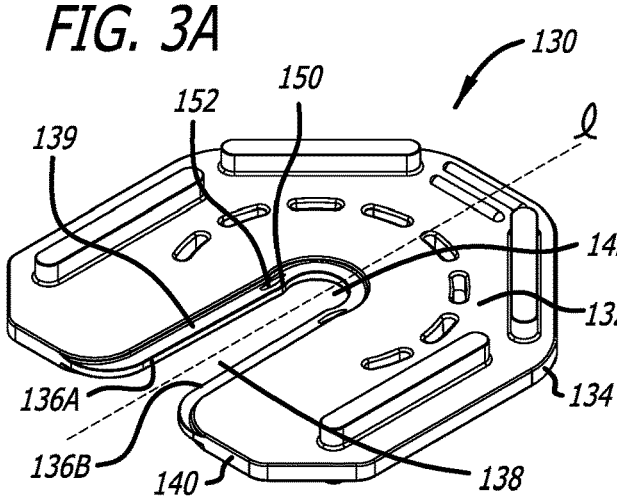
FIG. 3C is a perspective view of the clip of FIG. 3A.
Figure 3D:
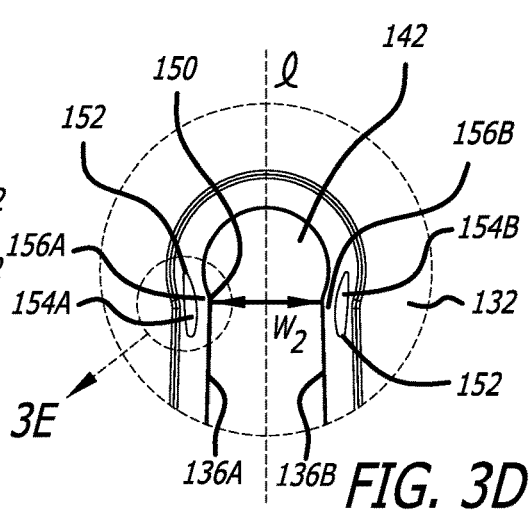
FIG. 3D illustrates a portion of the clip of FIG. 3A enlarged for magnification purposes.

With continued reference to FIGS. 3A-3F, the present invention overcomes the challenges associated with the valve holder no becoming stuck or difficult to remove from the clip 130 as a result of the interference fit by incorporating a compliance feature 152 in the interreference-fit area 150. With particular reference to FIG. 3D, the compliance feature 152 can comprise a cutout 154A, 154B adjacent to at least one of the opposing inner edges 136A, 136B such that the at least one of the opposing inner edges 136A, 136B defines a beam 156A, 156B within the interference-fit area 150. In the example shown, the compliance feature 152 includes a cutout 154A, 154B adjacent each of the opposing inner edges 136A, 136B such that each of the opposing inner edges 136A, 136B defines a beam 156A, 156B within the interference-fit area 150. The compliance feature 152 allows the beams 156A, 156B to deform (as illustrated by the phantom beam in FIGS. 3E and 3F), which reduces the force needed to push the shaft 112 of the valve holder no past the interference-fit area 150, and increases the tolerance range of the interference width for a given range of interference forces.

The shape of the cutout 154A, 154B and the beam 156A, 156B, as well as the average beam width $W_3$, will depend on the application and the range of acceptable interference forces, as well as on the materials used to form the clip 130 and the valve holder 110. In one embodiment, the clip 130 can comprise a molded polymer, such as a high-density polyethylene or an acetal resin or a polyoxymethylene, such as DELRIN® (manufactured by Dupont).

Figure 3E:
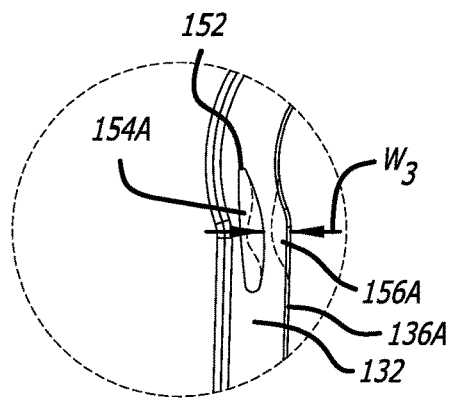
FIG. 3E illustrates a portion of the view of FIG. 3D enlarged for magnification purposes, and depicts a detailed view of a simply-supported beam defined by one of the opposing inner edges of the clip.
Figure 3F:
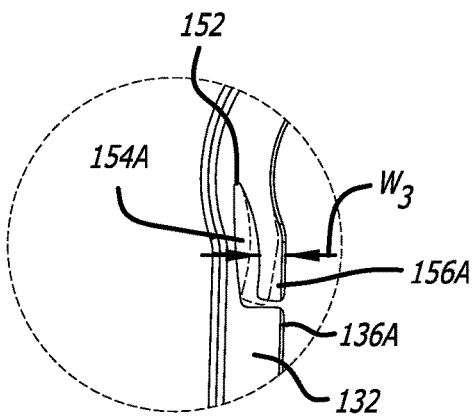
FIG. 3F illustrates an alternative embodiment of the portion of the view of FIG. 3D enlarged for magnification purposes, and depicts a detailed view of a cantilevered beam defined by one of the opposing inner edges of the clip.

In some embodiments, the cutout 154A, 154B can be oblong, and can be symmetrical or asymmetrical. For example, the cutout 154A, 154B can have an elliptical, rectangular, rounded rectangular, or stadium shape. The beam 156A, 156B defined by each of the opposing inner edges 136A, 136B can be a fixed beam, a simply-supported beam, or a cantilevered beam. FIG. 3E illustrates a cutout 154A having a rounded rectangular-shape, adjacent to the inner edge 136A, such that the inner edge 136A defines a simply-supported beam 156A. FIG. 3F illustrates an alternative embodiment in which the cutout 154A further includes a portion that extends through the inner edge 136A to the slot 138 such that the inner edge 136A defines a cantilevered beam. In one embodiment, the beam 156A can have an average beam width $W_3$ from about 0.5 mm to about 2 mm.

Figure 5:
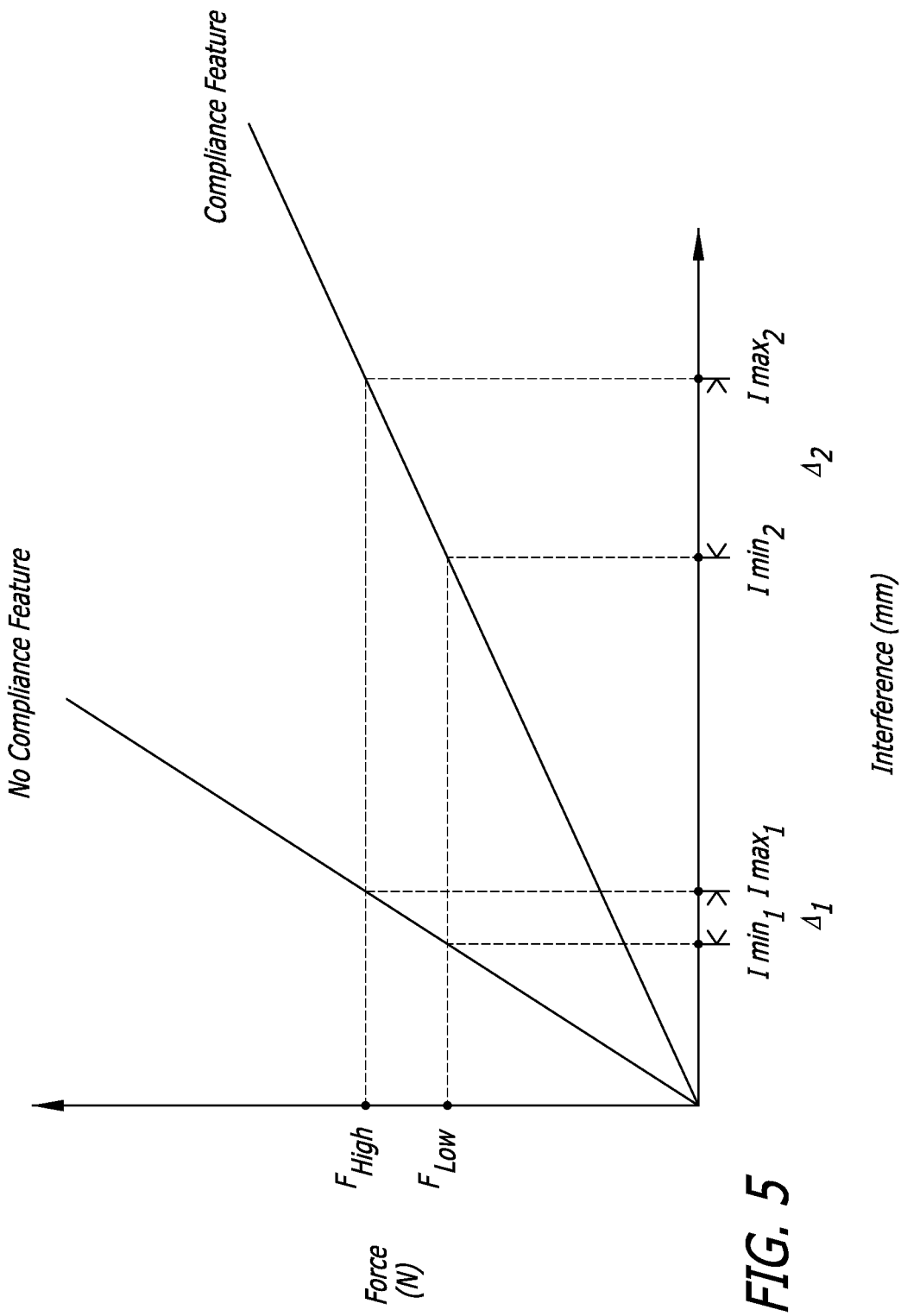
FIG. 5 is a graph illustrating the relationship between interference force and interference width in a clip having no compliance feature and, in another, a clip having a compliance feature in accordance with one embodiment.

The graph in FIG. 5 illustrates the impact that a compliance feature 152 can have on the relationship between the interference force and the interference width. As is shown, the slope for a clip having no compliance feature is steep; and the range Δ1 between a minimum interference width $I_{min1}$ and a maximum interference width $I_{max1}$—to produce a desired range of acceptable forces between $F_{Low}$ and $F_{High}$—is small. On the other hand, the compliance feature 152 reduces the slope and increases the range $\Delta_2$ between the minimum interference width $I_{min2}$ and the maximum interference width $I_{max2}$—to produce the same desired range of acceptable forces between $F_{Low}$ and $F_{High}$.

While the two exemplary curves in FIG. 5 are shown as lines, the relationship between the interference force and the interference width is not necessarily linear. Nevertheless, a line of best fit can be produced for a non-linear relationship, and the addition of a compliance feature 152 to the clip 110 will reduce the slope of this line and broaden the tolerance of the interference width needed to produce interference forces within a desired range.

With the bioprosthetic heart valve 10 secured to the valve holder no and with the valve holder 110 secured to the clip 130, the sub-assembly 100 can be placed into a container for further processing, storage, and transportation. In some embodiments (not shown), the sub-assembly 100 can be used with a bioprosthetic heart valve 10 that is stored in a preservative solution, such as glutaraldehyde. For these cases, the sub-assembly 100 can be configured to fit closely within a fluid-tight shipping jar, which is filled with preserving solution and sealed with a suitable lid, as described, for example, by U.S. Pat. No. 9,295,539. In other embodiments, the sub-assembly 100 can be used with a dehydrated or dry bioprosthetic heart valve 10 that is stored in dry packaging, as described, for example, by U.S. Pat. No. 9,539,080.

Figure 6:
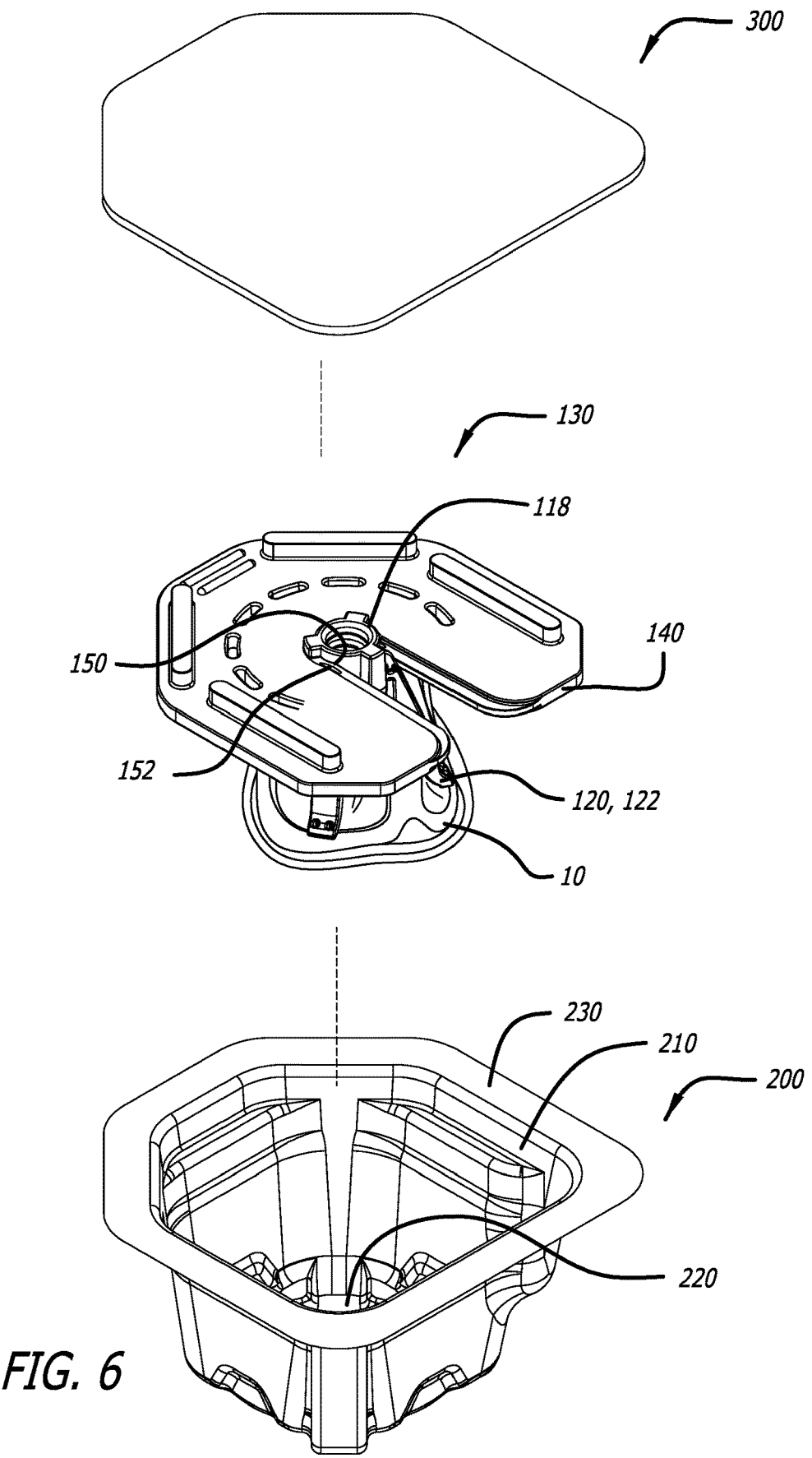
FIG. 6 illustrates an assembled heart valve holder and clip sub-assembly being inserted into a storage tray in accordance with one embodiment.
Figure 7:
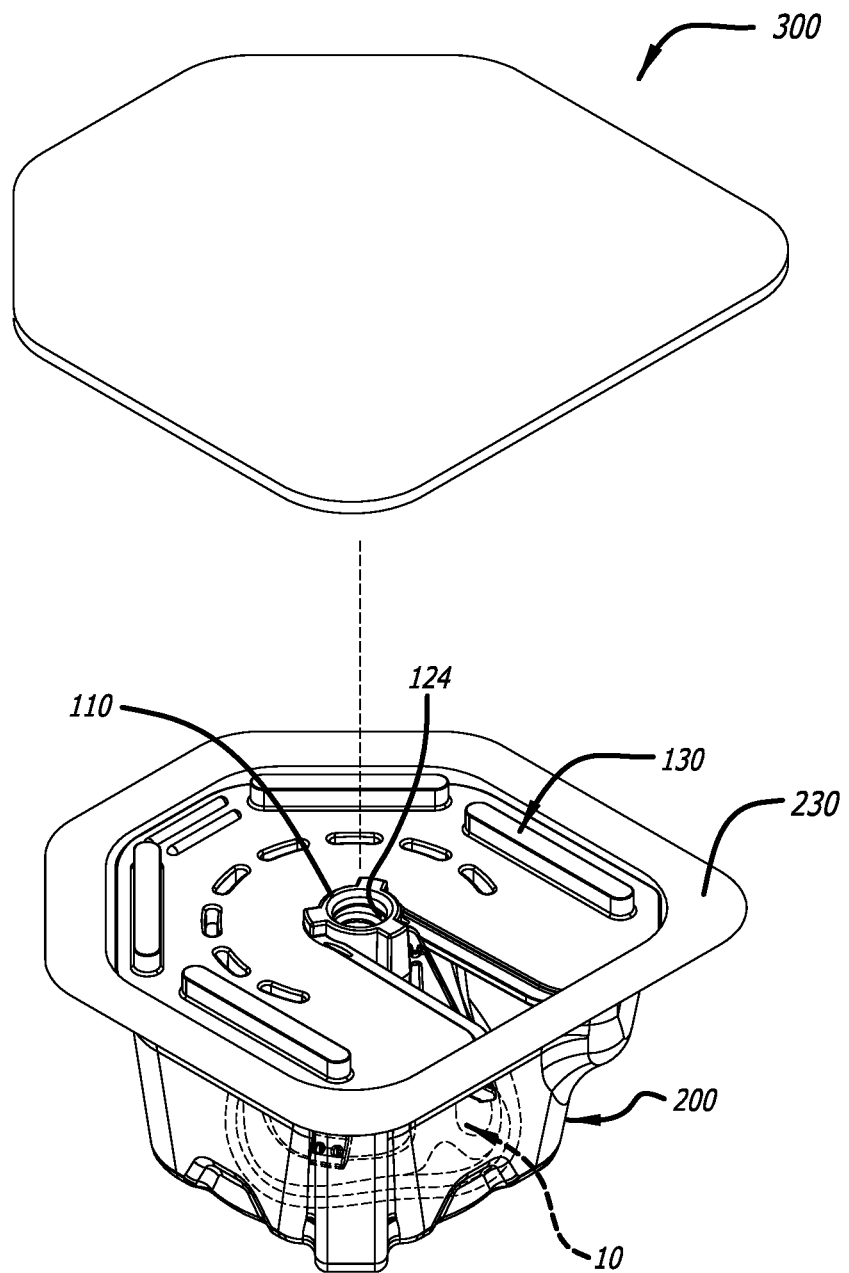
FIG. 7 illustrates a heart valve holder and clip subassembly placed within a cavity of a storage tray, and a gas-permeable lid for sealing over an upper surface of the tray, in accordance with one embodiment.

For instance, with reference now to FIGS. 6 and 7, the bioprosthetic heart valve 10 and the engagement structure 120 of the valve holder 110 can be lowered into a cavity 220 of a storage tray 200, and the clip 130 can sit on a stepped ledge 210 of the storage tray 200 such that the clip 130 caps the cavity 220 of the storage tray 200. In one embodiment, the clip 130 can engage the storage tray 200 in a non-rotating matter, allowing the valve holder no to be held stationary in the storage tray 200 while a user couples a threaded handle to the threaded bore 124 of the valve holder 110. The clip 130 is preferably formed to have a shape that corresponds with the shape of the storage tray 200 (or other container). Thus, while the clip 130 is depicted as an irregular hexagon, it should be understood that the clip 130 can be molded or otherwise formed to have a periphery that is round, square, rectangular, or any shape that is appropriate for a desired container. With the sub-assembly 100 in place within the storage tray 200, a gas-permeable lid 300 having an outer band of adhesive (not shown) can be sealed over the upper surface 230 of the storage tray 200.

Figure 8:
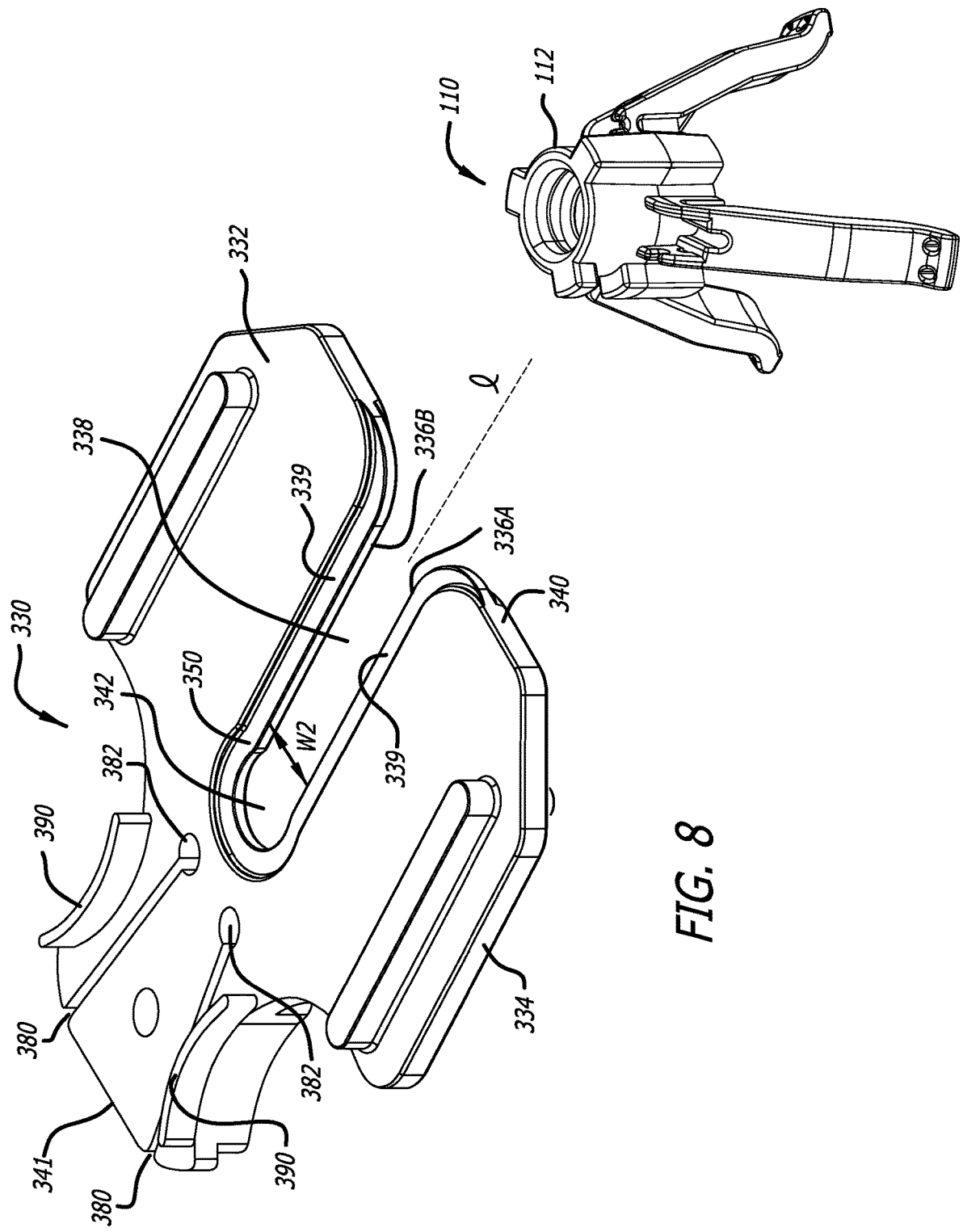
FIG. 8 is a perspective view of another embodiment of a clip and valve holder that can be used in connection with the storage tray.
Figure 9:
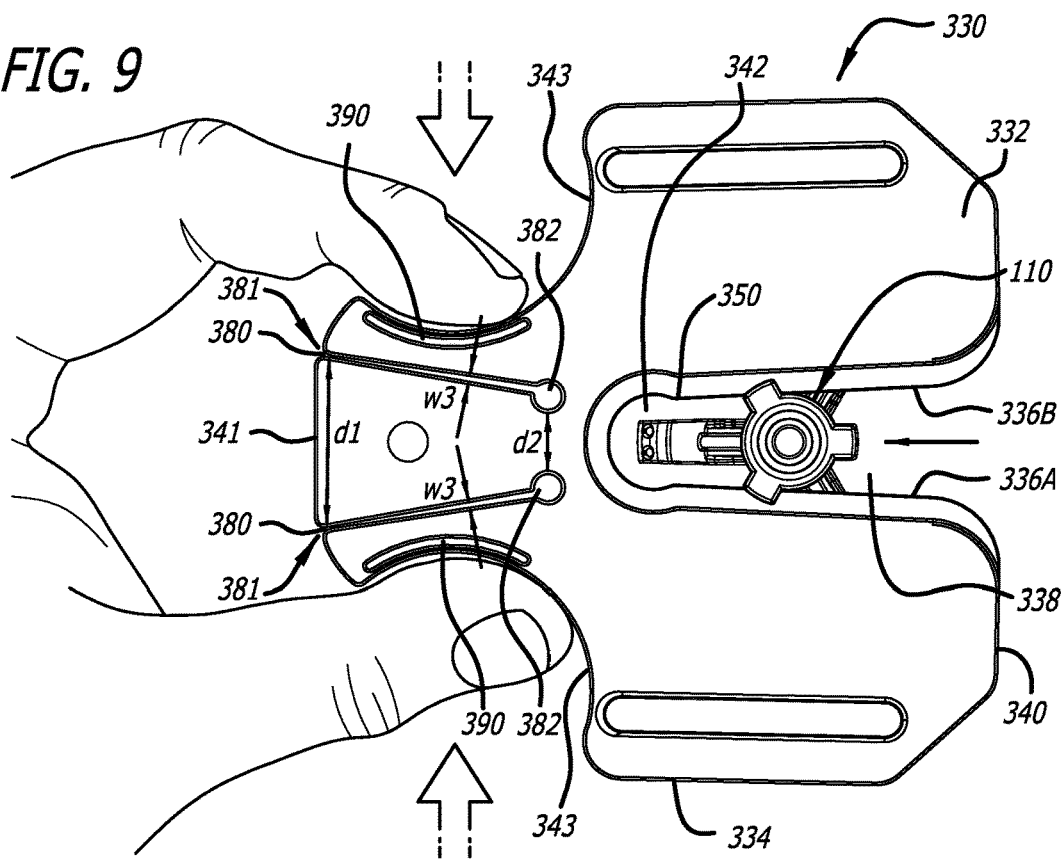
FIG. 9 is a top orthogonal view of the clip depicted in FIG. 8 in which the holds are compressed together to permit easy insertion or release of the valve holder shaft to or from the terminal docking end.
Figure 10:
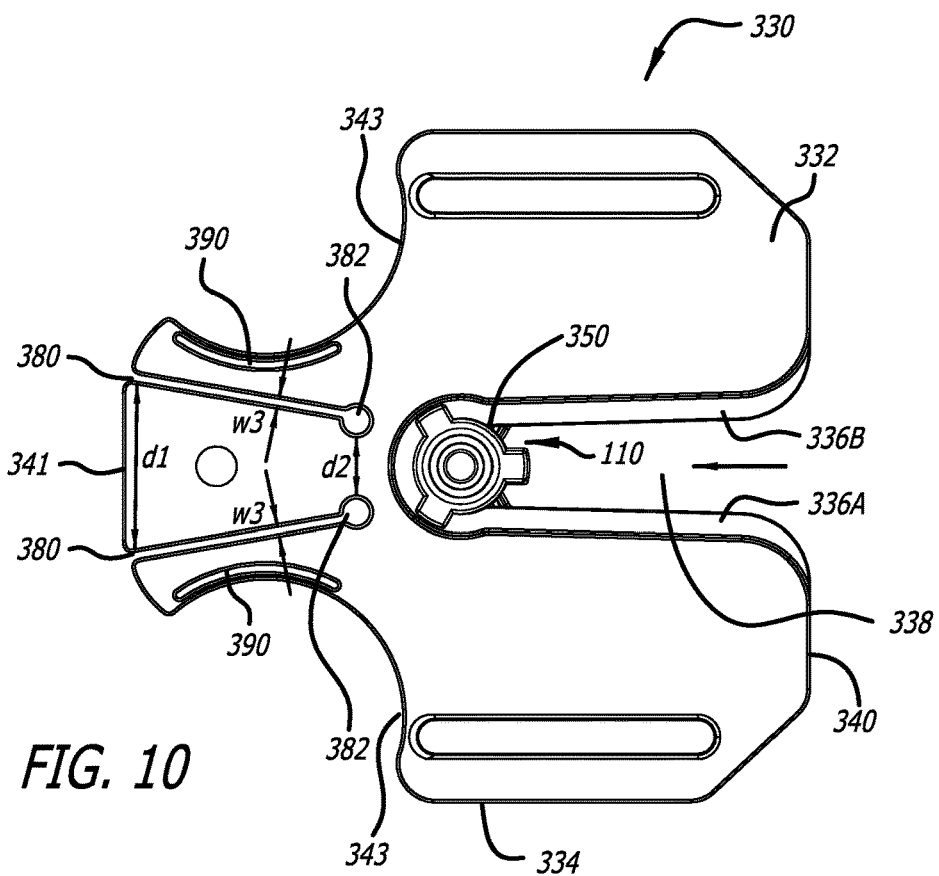
FIG. 10 is a top orthogonal view of the clip depicted in FIG. 8 in which the holds are released to secure the valve holder shaft within the terminal docking end.

With reference now to FIGS. 8-10, another embodiment of a clip 330 is provided that can be used with the valve holder 110 and storage tray 200 in a manner similar to the one depicted and described in relation to FIGS. 1, 4, 6 and 7. Similar to the embodiment of the clip 130 depicted in FIGS. 1, 4, 6, and 7, the clip 330 can retain the shaft 112 of the valve holder 110 by way of an interference fit. The clip 330 can comprise a body 332 having an outer periphery 334 and opposing inner edges 336A, 336B. The body 332 can be substantially planar and the opposing inner edges 336A, 336B can define a passageway 338 in the body 332 for receiving the shaft 112 of the valve holder 110. The passageway 338 can be open at a first end 340 of the body 332 and can extend along a longitudinal axis 1 of the body 332 from the first end 340 to a terminal docking end 342. One or both of the terminal docking end 342 and the passageway 338 can also comprise a stepped ledge 339 onto which a first end 114 of the shaft 112 can rest. As depicted in FIG. 2, a portion of the first end 114 of the shaft 112 protrudes radially outwardly of the shaft 112 such that it can rest on top of the stepped ledge 339.

In one embodiment, the passageway 338 can include an interference-fit area 350 adjacent to the terminal docking end 342. The interference-fit area 350 can be the same or similar to the one described in relation to FIGS. 1, 3, 4, 6, and 7 or can simply be a narrowed area. For example, a passageway width $W_2$ between the opposing inner edges 336A, 336B of the body 332 can decrease from the first end 340 of the body 332 to the dinterference-fit area 350. In one embodiment, the passageway width $W_2$ of the interference-fit area 350 can be narrower than the valve holder's 110 shaft width $W_1$. As such, when the shaft 112 of the valve holder 110 is pushed inward along the passageway 338 (as illustrated in FIG. 9), the shaft 112 will push against the opposing inner edges 336A, 336B in the interference-fit area 350 before snapping into (or out of) the terminal docking end 342. In one embodiment, the interference width, which is the difference between the shaft width $W_1$ and the passageway width $W_2$ of the interference-fit area 350 can be in the range of about 5 μm or more, about 10 μm or more, about 15 μm or more, about 20 μm or more, about 25 μm or more, about 30 μm or more, about 35 μm or more, about 40 μm or more, about 45 μm or more, about 50 μm or more, about 55 μm or more, about 60 μm or more, about 65 μm or more, about 70 μm or more, about 75 μm or more, about 80 μm or more, about 85 μm or more, about 90 μm or more, about 95 μm or more, about 100 μm or more, about 105 μm or more, about 110 μm or more, about 115 μm or more, about 120 μm or more, or about 125 μm or more. The interference width can also be in a range including and within any two of the foregoing values.

The clip 330 can include a release mechanism which can increase the distance between the opposing inner edges 336A, 336B or increase the passageway width $W_2$ of the interference-fit area 350 to allow easy insertion and removal of the valve holder 110 into and from the terminal docking end 342. The release mechanism can be effectuated by a pinch-to-release mechanism as depicted in FIGS. 9 and 10. The pinch-to-release mechanism can comprise one or more slots 380 having open ends disposed from a second end 341 of the body 332 and extending substantially towards the terminal docking end 342. In the embodiment depicted in FIGS. 8-10, the first 340 and second 341 ends are opposing edges of the body 332 of the clip 330. The two slots 380 can extend at an angle from the open ends 381 and towards the terminal docking end 342. Thus, as depicted in FIGS. 8-10, where two slots are provided, the distance $d_1$ between open ends 381 of the slots 380 can be greater than the distance $d_2$ between the slot ends 382.

The one or more slots 380 can have the same width or varying widths. While the embodiment in FIGS. 8-10 depicts a pair of slots as having substantially the same width $W_3$, it is understood that an embodiment can also comprise a single slot or two or more slots having the same or varying widths. The one or more slots 380 can be provided between a pair of holds 390 provided at the peripheral edges 343 of the body 332. The peripheral edge 343 can extend between the first 340 and second 341 ends of the body 332 in a straight line or in a curved and contoured shape as depicted in FIGS. 8-10. The holds 390 can be pinched together to decrease the widths $W_3$ of the one or more slots 390 (see FIG. 9) which, in turn, can increase the passageway width $W_2$ to facilitate easy insertion and removal of the valve holder's shaft 112 into and out of the terminal docking end 342 with less force. The widths $W_3$ of the one or more slots 380 may be decreased more substantially at the open ends 380 than at the area near the slot ends 382 when the holds 390 are compressed together. Once the holds 390 are pinched together, the force required to slidably move the valve holder no from the terminal docking end 342 and through passageway 338 to remove it from the clip 330 is less than 10 N, less than 9 N, less than 8 N, less than 7 N, less than 6 N, less than 5 N, less than 4 N, less than 3 N, less than 2 N, or less than 1 N. The one or more slots 380 can provide for a more secure fixation of the valve holder 110 and a larger dimensional tolerance.

Again, the interference-fit area 350 is provided to maintain the valve holder 110 within the terminal docking end 342 during processing, storage, and shipment—until the valve holder 110 is deliberately removed by the physician. The interference-fit area 350 should maintain the valve holder 110 in the terminal docking end 342 during transportation, and also allow for the easy removal of the valve holder no in the operating theater. The interference-fit area may be provided in a manner depicted and described with reference to FIGS. 1-7.

Figure 14:
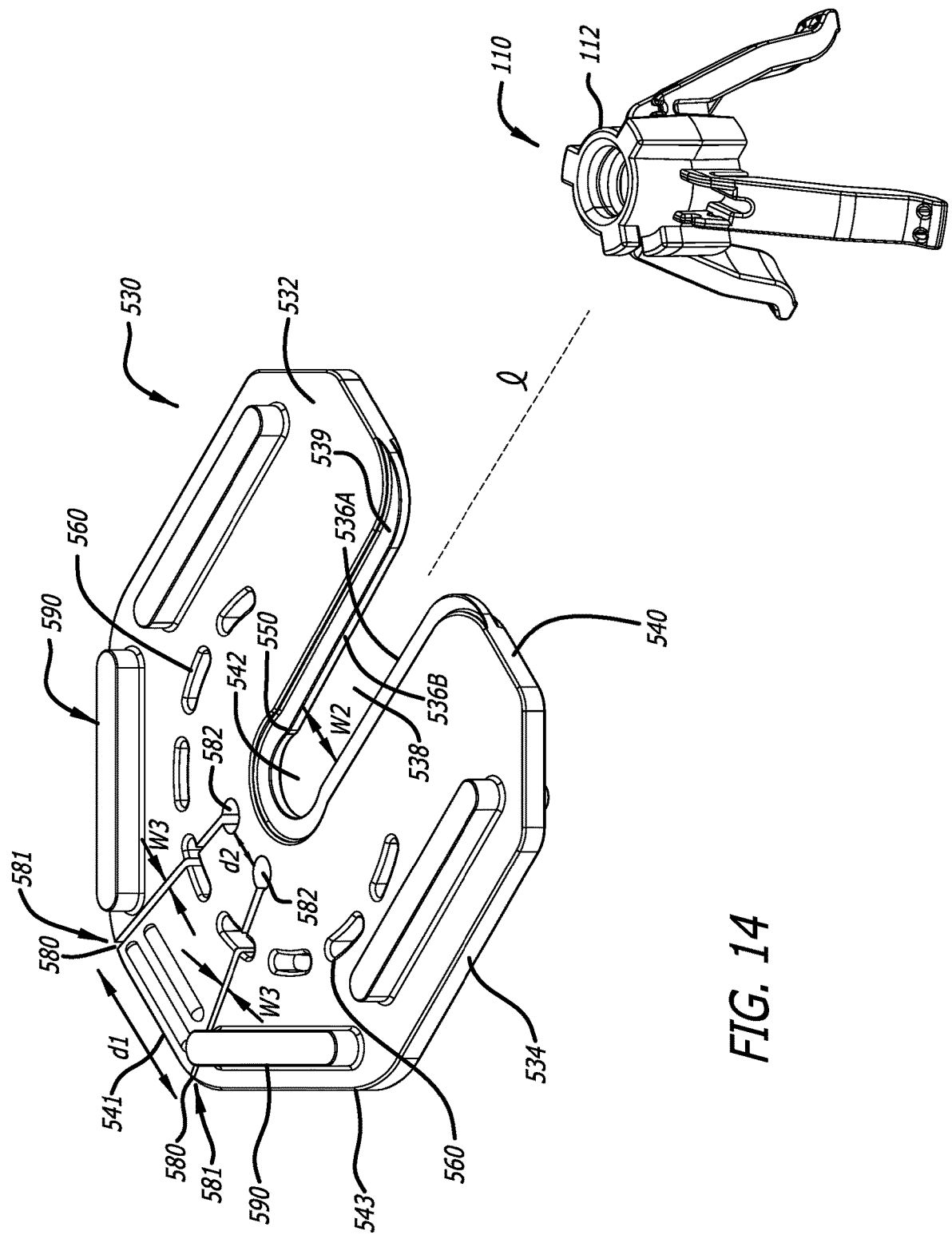
FIG. 14 is a perspective view of a further embodiment of the clip and valve holder that can be used in connection with the storage tray.
Figure 15:
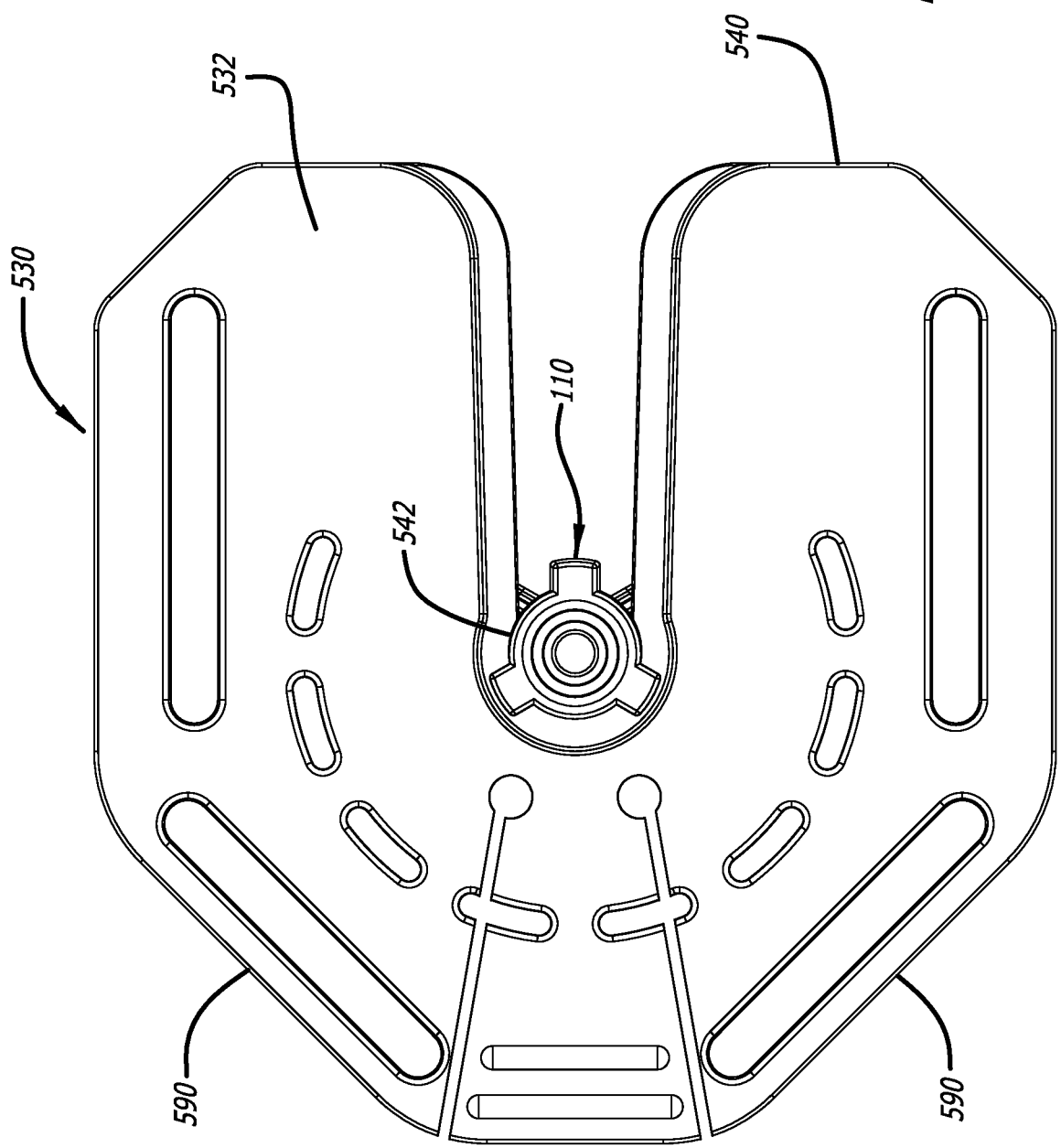
FIG. 15 is a top orthogonal view of the clip depicted in FIG. 15.

With reference now to FIGS. 14-15, yet a further embodiment of a clip 530 is provided that can be used with the valve holder no and storage tray 200 in a manner similar to the ones depicted and described in relation to FIGS. 1, 6, 7, and 8-10. Similar to the embodiment of the clip 330 depicted in FIGS. 8-10, the clip 530 can retain the shaft 112 of the valve holder 110 by way of an interference fit. The clip 530 can comprise a body 532 having an outer periphery 534 and opposing inner edges 536A, 536B. The body 532 can be substantially planar and the opposing inner edges 536A, 536B can define a passageway 538 in the body 532 for receiving the shaft 112 of the valve holder 110. The passageway 538 can be open at a first end 540 of the body 532 and can extend along a longitudinal axis l of the body 532 from the first end 540 to a terminal docking end 542. One or both of the terminal docking end 542 and the passageway 538 can also comprise a stepped ledge 539 onto which a first end 114 of the shaft 112 can rest. As depicted in FIG. 2, a portion of the first end 114 of the shaft 112 protrudes radially outwardly of the shaft 112 such that it can rest on top of the stepped ledge 539.

In one embodiment, the passageway 538 can include an interference-fit area 550 adjacent to the terminal docking end 542. The interference-fit area 550 can be the same or similar to the one described in relation to FIGS. 1, 3, 4, 6, 7, and 8-10 or can simply be a narrowed area. For example, a passageway width $W_2$ between the opposing inner edges 536A, 536B of the body 532 can decrease from the first end 540 of the body 532 to the interference-fit area 550. In one embodiment, the passageway width $W_2$ in the interference-fit area 550 can be narrower than the valve holder's no shaft width $W_1$. As such, when the shaft 112 of the valve holder 110 is pushed inwardly along the passageway 538 (as illustrated in FIG. 9), the shaft 112 will push against the opposing inner edges 536A, 536B in the interference-fit area 550 before snapping into (or out of) the terminal docking end 542. In one embodiment, the interference width, which is the difference between the shaft width $W_1$ and the passageway width $W_2$ of the interference-fit area 550 can be in the range of about 5 μm or more, about 10 μm or more, about 15 μm or more, about 20 μm or more, about 25 μm or more, about 30 μm or more, about 35 μm or more, about 40 μm or more, about 45 μm or more, about 50 μm or more, about 55 μm or more, about 60 μm or more, about 65 μm or more, about 70 μm or more, about 75 μm or more, about 80 μm or more, about 85 μm or more, about 90 μm or more, about 95 μm or more, about 100 μm or more, about 105 μm or more, about 110 μm or more, about 115 μm or more, about 120 μm or more, or about 125 μm or more. The interference width can also be in a range including and within any two of the foregoing values.

The clip 530 can include a release mechanism which can increase the distance between opposing inner edges 536A, 536B to allow easy insertion and removal of the valve holder no into and from the terminal docking end 542. The release mechanism can be effectuated by a pinch-to-release mechanism similar to the one depicted in FIGS. 9 and 10. Similar to the embodiment depicted in FIGS. 9 and 10, the pinch-to-release mechanism can comprise one or more slots 580 having open ends disposed from a second end 541 of the body 532 and extending substantially towards the terminal docking end 542. Furthermore, similar to the embodiment depicted in FIGS. 8-10, the first 540 and second 541 ends are opposing edges of the body 532 of the clip 530. The two slots 580 can extend at an angle from the open ends 581 and towards the terminal docking end 542. Thus, similar to the embodiment depicted in FIGS. 8-10, where two slots are provided, the distance $d_1$ between open ends 581 of the slots 580 can be greater than the distance $d_2$ between the slot ends 582.

The one or more slots 580 can have the same width or varying widths. While the embodiment in FIGS. 14-15 depicts a pair of slots as having substantially the same width $W_3$, it is understood that an embodiment can also comprise a single slot or two or more slots having the same or varying widths. The one or more slots 580 can be provided between a pair of holds 590 provided on the body 532. The holds 590 can be a protrusion from the body 532 that allows a finger grip to compress the holds 590 together to decrease the widths $W_3$ of the one or more slots 590 and increase the passageway width $W_2$, which facilitates easy insertion and removal of the valve holder's shaft 112 into and out of the terminal docking end 542 with less force in a manner similar to the embodiment depicted in FIG. 9. Alternatively, the holds 590 can also simply be the peripheral edge 543 that extends between the first 540 and second 541 ends. Once the holds 590 are pinched together, the force required to slidably move the valve holder no from the terminal docking end 541 and through passageway 538 to remove it from the clip 530 is less than 10 N, less than 9 N, less than 8 N, less than 7 N, less than 6 N, less than 5 N, less than 4 N, less than 3 N, less than 2 N, or less than 1 N. The one or more slots 580 can provide for a more secure fixation of the valve holder no and a larger dimensional tolerance.

As with the embodiment of the clip depicted in FIGS. 1, 3, 4, 6, and 7, the clip 530 can further include a plurality of openings 560 disposed within the body 532 to further decrease the force required to slidably move the valve holder no from the terminal docking end 542 and through passageway 538 to remove it from the clip 530. The plurality of openings 560 can be formed in any number of shapes (e.g. circular, oval, ovaline, rectilinear) and can be arranged in a variety of ways. In the embodiment depicted in FIGS. 1, 3, 4, 6, 7, 14 and 15, the plurality of openings is arranged around the terminal docking end 542. In alternative embodiments, the plurality of openings 560 can be arranged on one or both sides of the terminal docking end 542.

Again, the interference-fit area 550 is provided to maintain the valve holder 110 within the terminal docking end 542 during processing, storage, and shipment-until the valve holder no is deliberately removed by the physician. The interference-fit area 550 should maintain the valve holder no in the terminal docking end 542 during transportation, and also allow for the easy removal of the valve holder no in the operating theater. The interference-fit area may be provided in a manner depicted and described with reference to FIGS. 1-7 and 8-10.

Figure 11A:
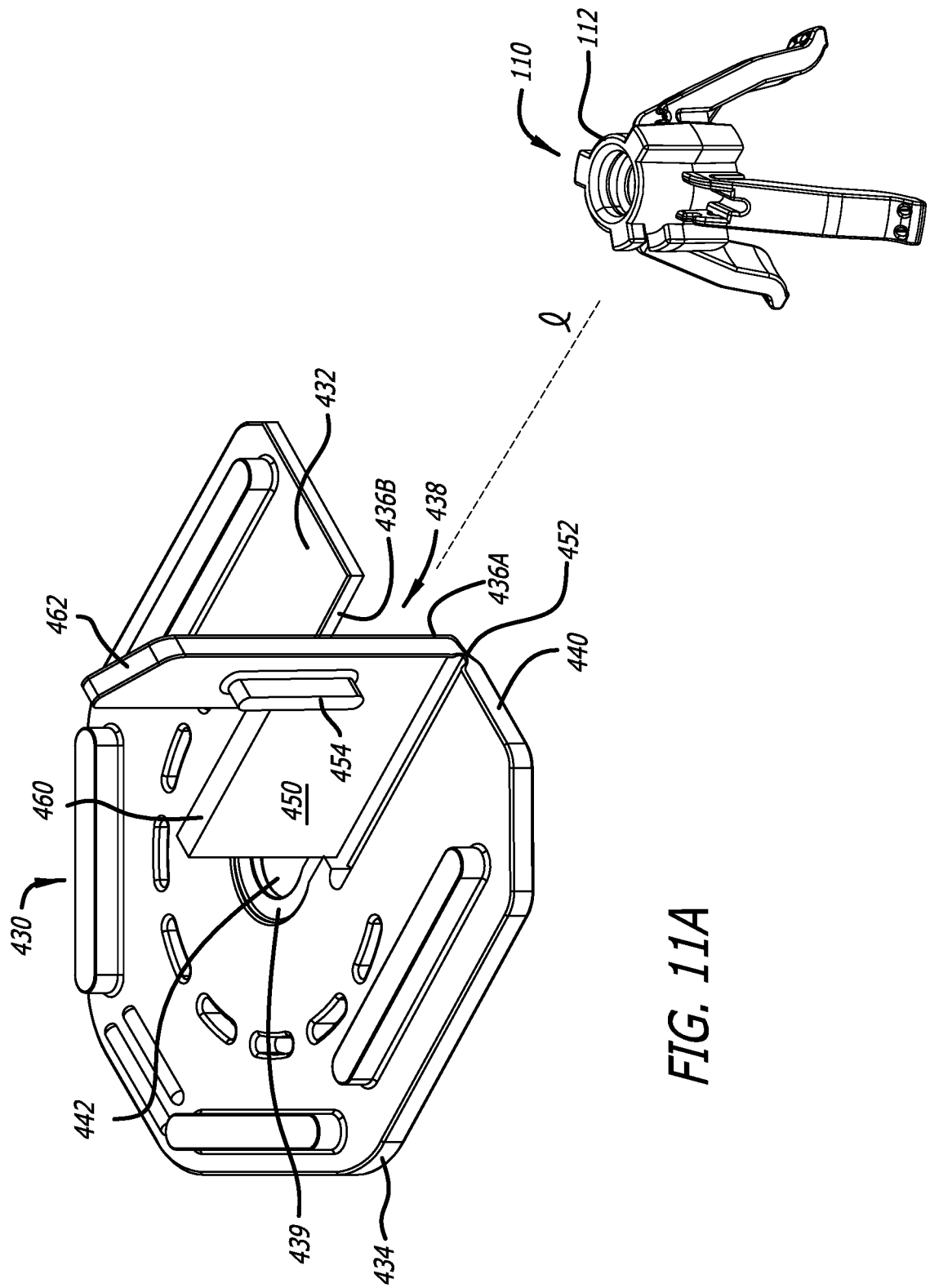
FIGS. 11A and 11B are perspective views from two sides of a further embodiment of a clip and valve holder that can be used in the storage tray.
Figure 11B:
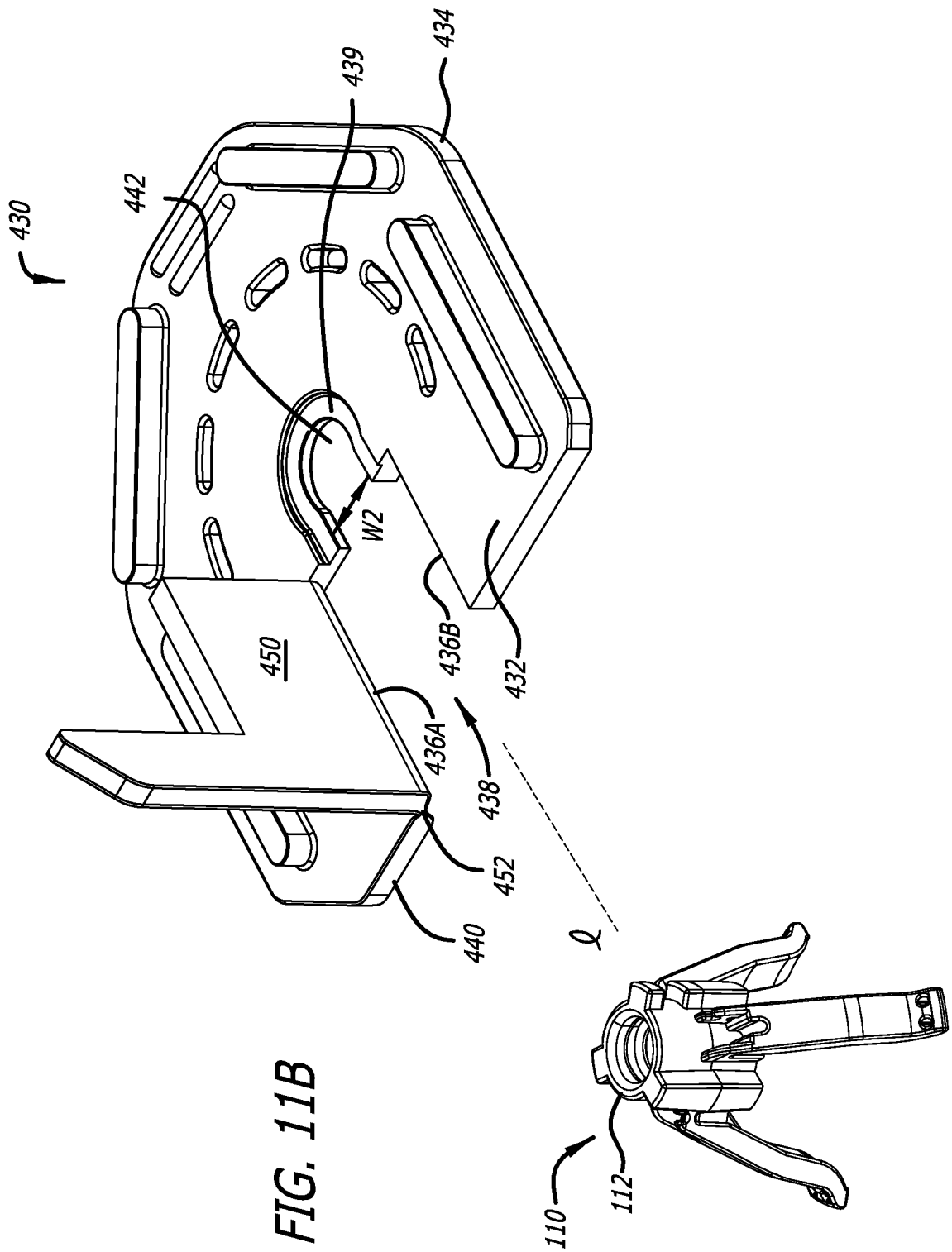
Figure 11C:
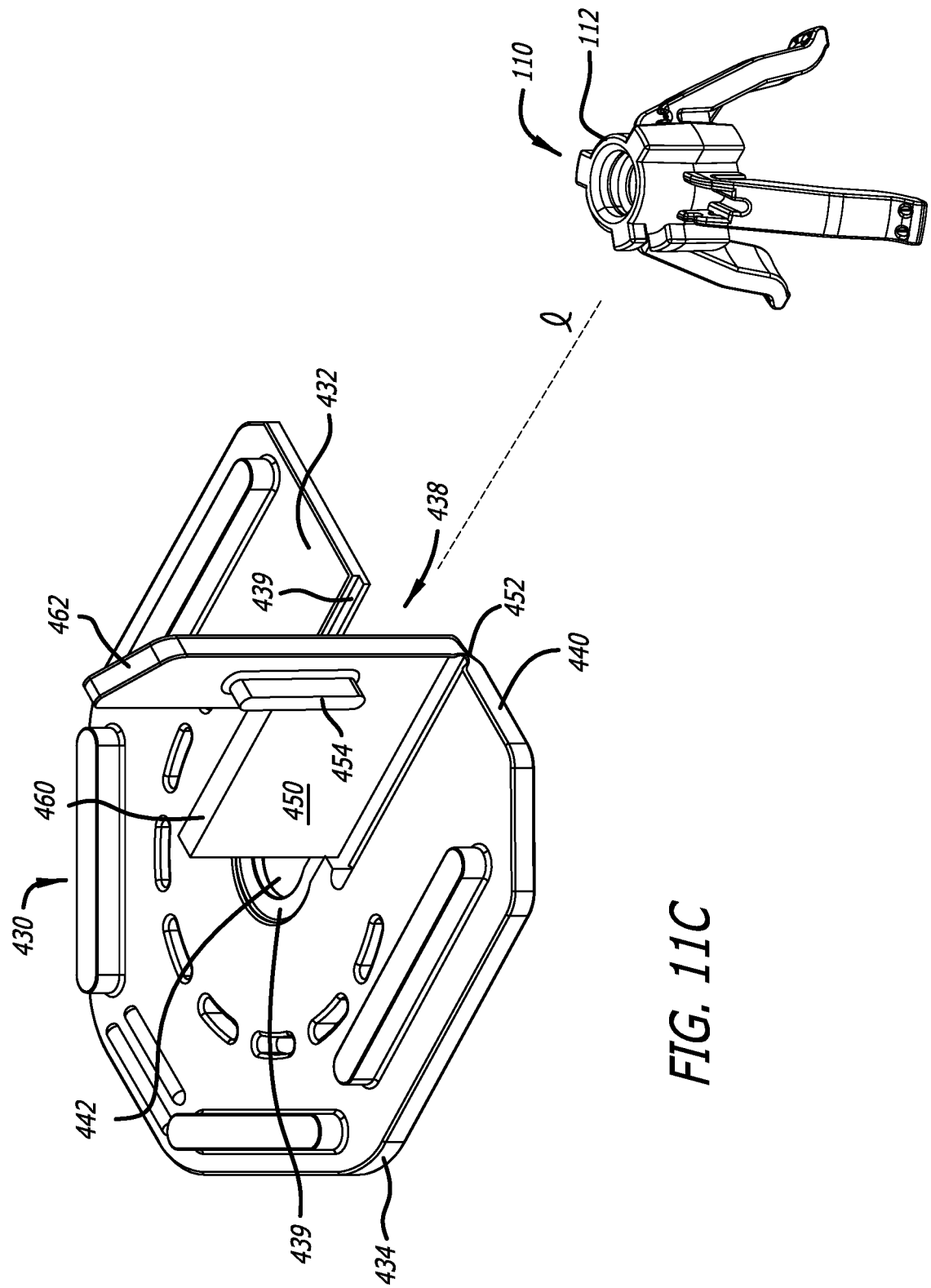
FIG. 11C is an alternate embodiment of the clip and valve holder depicted in FIGS. 11A and 11B having a stepped ledge to support the flap.
Figure 12:
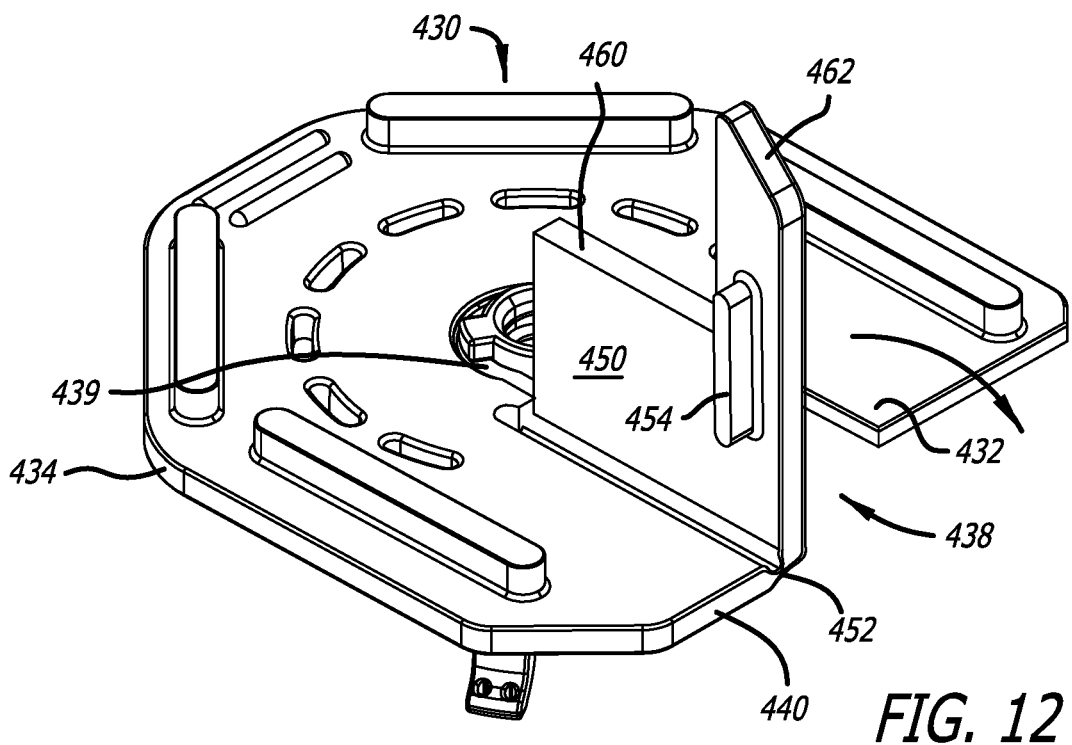
FIG. 12 is a perspective view of the clip depicted in FIGS. 11A and 11B showing the flap in the open position to permit easy insertion or release of the valve holder shaft to or from the terminal docking end.
Figure 13:
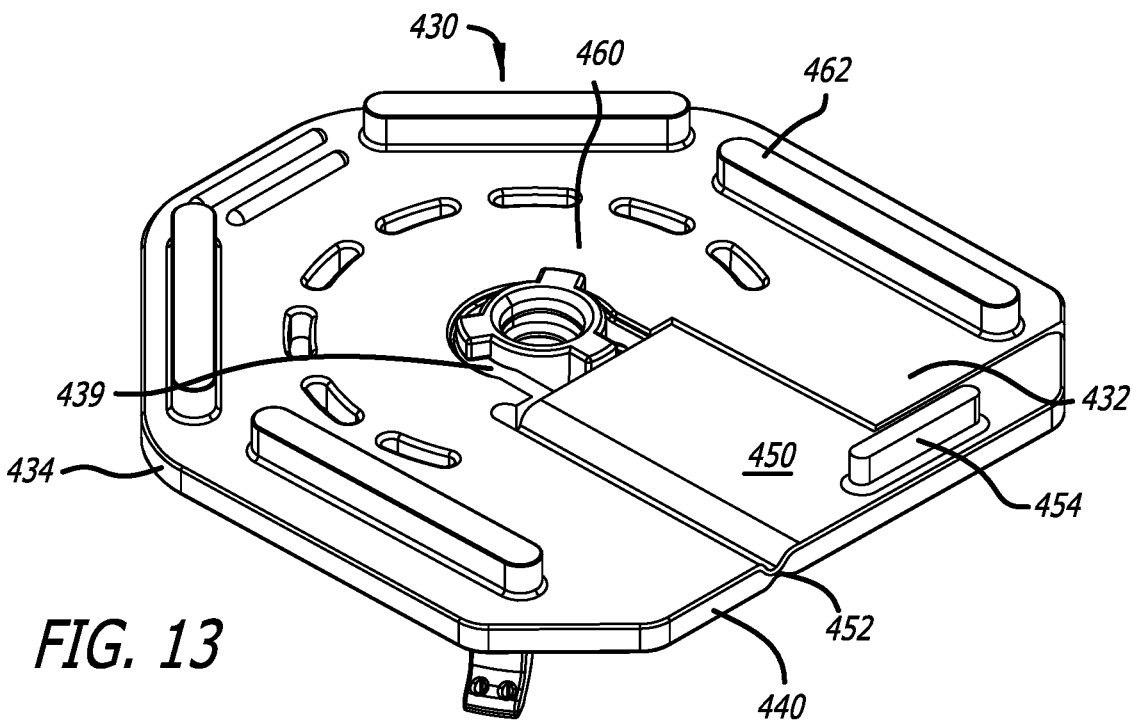
FIG. 13 is a perspective view of the clip depicted in FIGS. 11A and 11B showing the flap in the closed position to secure the valve holder shaft within the terminal docking end.

In accordance with another exemplary embodiment, a clip that can retain or secure a valve holder without requiring an interference fit is provided. With reference now to FIGS. 11-13, the clip 430 can comprise a body 432 having an outer periphery 434 and opposing inner edges 436A, 436B. The body 432 can be substantially planar and the opposing inner edges 436A, 436B can define a passageway 438 in the body 432 for receiving the shaft 112 of the valve holder 110. The passageway 438 can be open at a first end 440 of the body 432 and can extend along a longitudinal axis l of the body 432 from the first end 440 to a terminal docking end 442. One or both of the terminal docking end 442 and the passageway 438 can optionally also comprise a stepped ledge 439, as depicted in FIG. 11C, onto which a first end 114 of the shaft 112 can rest. As depicted in FIG. 2, a portion of the first end 114 of the shaft 112 protrudes radially outwardly of the shaft 112.

The clip 430 can further comprise a flap 450 that is coupled to the body 432. The flap 450 can be actuated between an open position (FIGS. 11A, 11B, 11C and 12) and a closed position (FIG. 13) via a hinge 452. In the open position depicted in FIGS. 11A, 11B, 11C and 12, the shaft 112 of the valve holder no can freely slide in the passageway 438 and be positioned in the terminal docking end 442 of the body 432. Once positioned at the terminal docking end 442, the flap 450 can be actuated in the closed position, as depicted in FIG. 13 to secure the valve holder within the clip 430.

The flap 450 can be sized and shaped to cover or block at least a portion of the passageway 438 so as to secure the shaft 112 of the valve holder no at the terminal docking end 442 and prevent the shaft 112 from sliding out of the terminal docking end 442. In accordance with one aspect of the embodiment, the flap 450 can be sized to rest on top of the stepped ledge 439 shown in FIG. 11C to prevent it from over rotating or falling below the body 432. As depicted in the exemplary embodiment in FIGS. 11-13, the flap 450 can be shaped to include a stepped-in portion 460 covering a portion of the passageway 438 and a stepped-out portion 462 that conforms to at least a portion of the outer periphery 434. While the hinge depicted in FIGS. 11-13 is a living hinge 452, it is understood that the flap 450 can be coupled to the body 432 in any other way that permits the flap 450 to actuate between the open (FIGS. 11A, 11B and 12) and closed (FIG. 13) positions. The flap 450 can further comprise a protrusion 454 to allow grasping to open and close the flap 450.

In accordance with one aspect of this embodiment, the shaft 112 of the valve holder 110 can be retained within the terminal docking end without requiring an interference fit. In other words, the widths of either or both of the terminal docking end 442 and the passageway 438 need not be less than the valve holder's 100 shaft width $W_1$. In one embodiment, the widths of one or both of the passageway 438 or terminal docking end 442 is roughly equal to or slightly greater than the width of the shaft 112 of the valve holder 110. As such, minimal to no force would be required move the valve holder 110 through the passageway 438 and into or out of the terminal docking end 442. The force required to move the valve holder no through the passageway 438 and into the terminal docking end 442 can be 5 N or less, 4 N or less, 3 N or less, 2 N or less, or 1 N or less.

It should be appreciated from the foregoing description that the present invention provides an improved packaging assembly that provides an interference force within a desired range over a larger range of interference widths, thereby securely maintaining a bioprosthetic heart valve within the packaging system, while also allowing easy removal of the heart valve from the packaging system without damage or contamination.

Specific methods, devices, and materials are described, although any methods and materials similar or equivalent to those described can be used in the practice or testing of the present embodiment. Unless defined otherwise, all technical and scientific terms used herein have the same meanings as commonly understood by one of ordinary skill in the art to which this embodiment belongs.

The terms "a," "an," and "at least one" encompass one or more of the specified element. That is, if two of a particular element are present, one of these elements is also present and thus "an" element is present. The terms "a plurality of" and "plural" mean two or more of the specified element. The term "or" used between the last two of a list of elements means any one or more of the listed elements. For example, the phrase "A, B, or C" means "A, B, and/or C," which means "A," "B," "C," "A and B," "A and C," "B and C," or "A, B, and C." The term "coupled" generally means physically coupled or linked and does not exclude the presence of intermediate elements between the coupled items absent specific contrary language.

Without further elaboration, it is believed that one skilled in the art, using the proceeding description, can make and use the present invention to the fullest extent. The invention has been described in detail with reference only to the presently preferred embodiments. Persons skilled in the art will appreciate that various modifications can be made without departing from the invention. Accordingly, the invention is defined only by the following claims.

What is claimed is:

1. A packaging assembly for storing a bioprosthetic heart valve, the packaging assembly comprising:
   a valve holder configured to hold the bioprosthetic heart valve and comprising a shaft having a shaft width; and
   a clip configured to receive the shaft of the valve holder; wherein the clip comprises:
      a body having an outer periphery and opposing inner edges, the opposing inner edges defining a slot in the body for receiving the shaft of the valve holder, wherein the slot is open at a first end of the body and extends, with a varying slot width, along a longitudinal axis of the body, from the first end through an interference-fit area to a docking aperture; and
      a compliance feature in the interference-fit area of the slot adjacent to the docking aperture;
   wherein the slot width between the opposing inner edges of the body in the interference-fit area is less than the shaft width;
   wherein the slot width between the opposing inner edges of the body decreases from the first end of the body to the interference-fit area;
   wherein the compliance feature comprises a cutout adjacent to each of the opposing inner edges such that each of the opposing inner edges defines a beam within the interference-fit area; and
   wherein the beam defined by each of the opposing inner edges has two ends, each of which is fixed or simply-supported.

2. The packaging assembly of claim 1, wherein the body is substantially planar.

3. The packaging assembly of claim 1, wherein the two ends of the beam defined by each of the opposing inner edges are both fixed.

4. The packaging assembly of claim 1, wherein the cutout adjacent to each of the opposing inner edges is oblong.

5. The packaging assembly of claim 1, wherein the beam defined by each of the opposing inner edges has an average beam width from about 0.5 mm to about 2 mm.

6. The packaging assembly of claim 1, wherein the clip comprises a molded polymer.

7. The packaging assembly of claim 1, wherein the clip comprises a high-density polyethylene or an acetal resin.

8. The packaging assembly of claim 1, wherein the valve holder further comprises a cap coupled to a first end of the shaft and an engagement structure coupled to a second end of the shaft, wherein the engagement structure is configured to removably couple to the bioprosthetic heart valve.

9. The packaging assembly of claim 8, wherein the shaft separates the cap and the engagement structure.

10. The packaging assembly of claim 8, wherein the engagement structure comprises a plurality of legs.

11. The packaging assembly of claim 10, wherein the plurality of legs are outwardly and downwardly angled.

12. The packaging assembly of claim 1, further comprising a storage tray having a stepped ledge surrounding a cavity;
   wherein the body of the clip is shaped to rest on the stepped ledge of the storage tray in a non-rotatable manner.

13. The packaging assembly of claim 12, wherein the clip's body is shaped to rest on the stepped ledge of the storage tray such that the valve holder's engagement structure is suspended within the cavity of the storage tray when the valve holder is docked within the clip's docking aperture.

14. The packaging assembly of claim 12, further comprising a gas-permeable lid coupled to an upper surface of the storage tray.

15. The packaging assembly of claim 1, wherein the two ends of the beam defined by each of the opposing inner edges are both simply-supported.

16. The packaging assembly of claim 1, wherein:
   the body of the clip defines a plane; and
   the clip is thinner, in a direction normal to the plane, at the opposing inner edges of the body than at the outer periphery of the body.

17. The packaging assembly of claim 1, wherein:
   the body of the clip defines a plane; and
   the clip is thinner, in a direction normal to the plane, at the interference-fit area than at the outer periphery of the body.

18. The packaging assembly of claim 1, wherein:
   the body of the clip defines a plane; and
   the clip is thinner, in a direction normal to the plane, at the beam than at the outer periphery of the body.

19. The packaging assembly of claim 1, wherein the cutout adjacent to each of the opposing inner edges of the body has a fully closed shape.

20. The packaging assembly of claim 19, wherein the closed shape is a rounded rectangular shape.

21. A packaging assembly for storing a bioprosthetic heart valve, the packaging assembly comprising:
   a valve holder configured to hold the bioprosthetic heart valve and comprising a shaft having a shaft width;
   a clip configured to receive the shaft of the valve holder; and
   a storage tray having a stepped ledge surrounding a cavity;
   wherein the clip comprises:
      a body having an outer periphery and opposing inner edges, the opposing inner edges defining a slot in the body for receiving the shaft of the valve holder, wherein the slot is open at a first end of the body and extends, with a varying slot width, along a longitudinal axis of the body, from the first end through an interference-fit area to a docking aperture; and a compliance feature in the interference-fit area of the slot adjacent to the docking aperture;

wherein the slot width between the opposing inner edges of the body in the interference-fit area is less than the shaft width;

wherein the slot width between the opposing inner edges of the body decreases from the first end of the body to the interference-fit area;

wherein the compliance feature comprises a cutout adjacent to each of the opposing inner edges such that each of the opposing inner edges defines a beam within the interference-fit area;

wherein the body of the clip is shaped to rest on the stepped ledge of the storage tray in a non-rotatable manner.

22. A packaging assembly for storing a bioprosthetic heart valve, the packaging assembly comprising:

a valve holder configured to hold the bioprosthetic heart valve and comprising a shaft having a shaft width;

a clip configured to receive the shaft of the valve holder; and a storage tray having a stepped ledge surrounding a cavity;

wherein the clip comprises:

a body defining a plane and having an outer periphery and opposing inner edges, the opposing inner edges defining a slot in the body for receiving the shaft of the valve holder, wherein the slot is open at a first end of the body and extends, with a varying slot width, along a longitudinal axis of the body, from the first end through an interference-fit area to a docking aperture; and a compliance feature in the interference-fit area of the slot adjacent to the docking aperture;

wherein the slot width between the opposing inner edges of the body in the interference-fit area is less than the shaft width;

wherein the slot width between the opposing inner edges of the body decreases from the first end of the body to the interference-fit area;

wherein the compliance feature comprises a cutout adjacent to each of the opposing inner edges such that each of the opposing inner edges defines a beam within the interference-fit area;

wherein the clip is thinner, in a direction normal to the plane, at the opposing inner edges of the body than at the outer periphery of the body.

23. The packaging assembly of claim 22, wherein the clip is thinner, in the direction normal to the plane, at the interference-fit area than at the outer periphery of the body.

24. The packaging assembly of claim 22, wherein the clip is thinner, in the direction normal to the plane, at the beam than at the outer periphery of the body.

25. A packaging assembly for storing a bioprosthetic heart valve, the packaging assembly comprising:

a valve holder configured to hold the bioprosthetic heart valve and comprising a shaft having a shaft width; and a clip configured to receive the shaft of the valve holder;

wherein the clip comprises:

a body having an outer periphery and opposing inner edges, the opposing inner edges defining a slot in the body for receiving the shaft of the valve holder, wherein the slot is open at a first end of the body and extends, with a varying slot width, along a longitudinal axis of the body, from the first end through an interference-fit area to a docking aperture; and a compliance feature in the interference-fit area of the slot adjacent to the docking aperture;

wherein the slot width between the opposing inner edges of the body in the interference-fit area is less than the shaft width;

wherein the slot width between the opposing inner edges of the body decreases from the first end of the body to the interference-fit area;

wherein the compliance feature comprises a cutout adjacent to each of the opposing inner edges such that each of the opposing inner edges defines a beam within the interference-fit area;

wherein the cutout adjacent to each of the opposing inner edges of the body has a fully closed shape.

26. The packaging assembly of claim 25, wherein the fully closed shape is a rounded rectangular shape.

27. A packaging assembly for storing a bioprosthetic heart valve, the packaging assembly comprising:

a valve holder configured to hold the bioprosthetic heart valve and comprising a shaft having a shaft width; and a clip configured to receive the shaft of the valve holder;

wherein the clip comprises:

a body having an outer periphery and opposing inner edges, the opposing inner edges defining a slot in the body for receiving the shaft of the valve holder, wherein the slot is open at a first end of the body and extends, with a varying slot width, along a longitudinal axis of the body, from the first end through an interference-fit area to a docking aperture; and a compliance feature in the interference-fit area of the slot adjacent to the docking aperture;

wherein the slot width between the opposing inner edges of the body in the interference-fit area is less than the shaft width;

wherein the slot width between the opposing inner edges of the body decreases from the first end of the body to the interference-fit area;

wherein the compliance feature comprises a cutout adjacent to each of the opposing inner edges such that each of the opposing inner edges defines a beam within the interference-fit area;

wherein the beam defined by each of the opposing inner edges is a fixed beam or a simply-supported beam;

wherein the cutout adjacent to each of the opposing inner edges of the body has a closed shape; and wherein the closed shape is a rounded rectangular shape.

* * * * *